(12) United States Patent
Demin et al.

(10) Patent No.: US 8,436,036 B2
(45) Date of Patent: May 7, 2013

(54) DIARYL ETHERS

(75) Inventors: Samuel Dominique Demin, Mechelen (BE); David McGowan, Brussels (BE); Stefaan Julien Last, Lint (BE); Pierre Jean-Marie Bernard Raboisson, Rosieres (BE)

(73) Assignee: Janssen R&D Ireland, Little Island, Co Cork (IE)

( * ) Notice: Subject to any disclaimer, the term of this patent is extended or adjusted under 35 U.S.C. 154(b) by 5 days.

(21) Appl. No.: 13/265,588

(22) PCT Filed: Apr. 23, 2010

(86) PCT No.: PCT/EP2010/055482
§ 371 (c)(1),
(2), (4) Date: Oct. 21, 2011

(87) PCT Pub. No.: WO2010/122162
PCT Pub. Date: Oct. 28, 2010

(65) Prior Publication Data
US 2012/0034678 A1 Feb. 9, 2012

(30) Foreign Application Priority Data
Apr. 24, 2009 (EP) .................................. 09158676

(51) Int. Cl.
*A61K 31/4178* (2006.01)
*C07D 403/14* (2006.01)
(52) U.S. Cl.
USPC ................... 514/397; 548/300.1; 548/312.7; 514/385; 514/396
(58) Field of Classification Search ............... 548/300.1, 548/311.1, 312.7; 514/385, 396, 397
See application file for complete search history.

(56) References Cited

U.S. PATENT DOCUMENTS

| 8,088,368 B2 * | 1/2012 | Guo et al. .................... 424/85.4 |
| 8,273,341 B2 * | 9/2012 | Guo et al. .................... 424/85.4 |
| 2009/0186930 A1 | 7/2009 | Liberatore |

FOREIGN PATENT DOCUMENTS

| FR | 2 900 404 A | 11/2007 |
| WO | WO 00/57877 A | 10/2000 |
| WO | WO 2006/133326 A | 12/2006 |
| WO | WO 2007/117692 A | 10/2007 |
| WO | WO 2008/021927 A | 2/2008 |

OTHER PUBLICATIONS

Krieger, et al. "Enhancement of Hepatitis C Virus RNA Replication by Cell Culture-Adaptive Mutations", Journal of Virology, vol. 75, No. 10, pp. 4614-4624 (2001).
Lohmann, et al. "Replication of Subgenomic Hepatitis C Virus RNAs in a Hepatoma Cell Line", Science, vol. 285, pp. 110-113 (1999).

* cited by examiner

*Primary Examiner* — Golam M M Shameem
(74) *Attorney, Agent, or Firm* — Andrew Jo Kamage

(57) ABSTRACT

Compounds of the formula I:

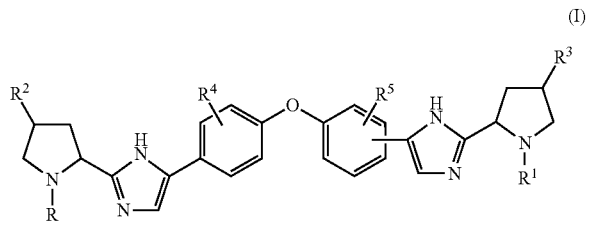

including any possible stereoisomers thereof, or a pharmaceutically acceptable salt and/or solvate thereof, as well as pharmaceutical formulations and the use of compounds of formula I as HCV inhibitors.

10 Claims, No Drawings

DIARYL ETHERS

This application is a national stage application of PCT/EP2010/055482, filed Apr. 23, 2010, which claims priority benefit of Application No. EP 09158676.8 filed Apr. 24, 2009. The complete disclosures of the aforementioned related patent applications are hereby incorporated herein by reference for all purposes.

TECHNICAL FIELD

This invention relates to diaryl ethers, which are inhibitors of the NS5A protein encoded by hepatitis C virus (HCV) and their use in the treatment or prophylaxis of HCV.

BACKGROUND ART

HCV is a single stranded, positive-sense RNA virus belonging to the Flaviviridae family of viruses in the hepacivirus genus. The viral genome translates into a single open reading frame that encodes for multiple structural and non-structural proteins.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis, leading to cirrhosis, end-stage liver disease, and HCC (hepatocellular carcinoma), making it the leading cause of liver transplantations.

There are six major HCV genotypes and more than 50 subtypes, which are differently distributed geographically. HCV genotype 1 is the predominant genotype in Europe and in the US. The extensive genetic heterogeneity of HCV has important diagnostic and clinical implications, perhaps explaining difficulties in vaccine development and the lack of response to current therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in 40% of patients infected by genotype 1 HCV and about 80% of those infected by genotypes 2 and 3. Beside the limited efficacy on HCV genotype 1, this combination therapy has significant side effects including influenza-like symptoms, hematologic abnormalities, and neuropsychiatric symptoms. Hence there is a need for more effective, convenient and better-tolerated treatments.

Experience with HIV drugs, in particular with HIV protease inhibitors, has taught that sub-optimal pharmacokinetics and complex dosing regimens quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design.

The NS5A protein of HCV is located downstream of the NS4B protein and upstream of the NS5B protein. Upon post-translational cleavage by the viral serine protease NS3, the NS5A matures into a zinc containing, three-domain phosphoprotein that either exists as a hypophosphorylated (56-kDa, p56) or hyperphosphorylated species (58-kDa, p58). NS5A of HCV is implicated in multiple aspects of the viral lifecycle including viral replication and infectious particle assembly as well as modulation of the environment of its host cell. Although no enzymatic function has been ascribed to the protein it is reported to interact with numerous viral and cellular factors.

A number of patents and patent applications disclose compounds with NS5A HCV inhibitory activity. WO2006/133326 discloses stilbene derivatives while WO 2008021927 discloses biphenyl derivatives having NS5A HCV inhibitory activity.

There is a need for HCV inhibitors that may overcome the disadvantages of current HCV therapy such as side effects, limited efficacy, the emerging of resistance, and compliance failures, as well as improve the sustained viral load response.

The present invention concerns a group of HCV inhibiting diaryl ethers with useful properties regarding one or more of the following parameters: antiviral efficacy, favorable profile of resistance development, lack of toxicity and genotoxicity, favorable pharmacokinetics and pharmacodynamics and ease of formulation and administration.

Compounds of the invention may also be attractive due to the fact that they lack activity against other viruses, in particular against HIV. HIV infected patients often suffer from co-infections such as HCV. Treatment of such patients with an HCV inhibitor that also inhibits HIV may lead to the emergence of resistant HIV strains.

DESCRIPTION OF THE INVENTION

In one aspect, the present invention provides compounds, which can be represented by the formula I:

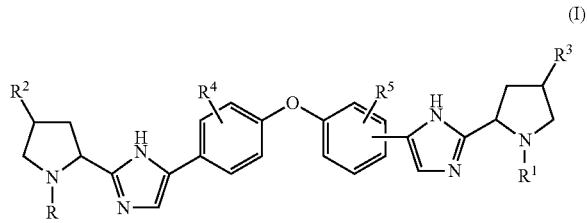

(I)

including any possible stereoisomers thereof, wherein:
R and $R^1$, independently from one another, are benzoyl optionally substituted with one, two or three substituents each independently selected from halo and $C_1$-$C_6$alkyl, or —C(=O)-Het wherein Het is optionally substituted with one or two substituents independently selected from $C_1$-$C_4$alkyl, or a group of formula —C(=O)—CH($R^x$)—$R^6$, benzyloxycarbonyl, $C_1$-$C_6$alkyloxycarbonyl, a group of formula $H_2N$—CH($R^7$)—C(=O)—, a group of formula $R^8$—O—C(=O)—HN—CH($R^7$)—C(=O)—, or —C(=O)—C(=O)-phenyl;
$R^6$ is $C_1$-$C_4$alkyl, $C_3$-$C_6$cylcoalkyl, benzyl or phenyl wherein the phenyl may be optionally substituted with one, two or three substituents each independently selected from halo, $C_1$-$C_6$alkyl, methoxy, trifluoromethoxy or two substituents on adjacent ring atoms, together with the phenyl ring, form a benzodioxole, and, wherein the $C_1$-$C_4$alkyl is optionally substituted with mono- or di$C_1$-$C_4$alkylamino, phenylsulphonyl, Het, and, wherein benzyl is optionally substituted with one, two or three substituents each independently selected from halo, methoxy;

$R^x$ is selected from hydrogen, hydroxy, $C_1$-$C_6$alkoxy, amino, mono- or di$C_1$-$C_6$alkyl-amino, pyrrolidinyl, piperidinyl, morpholinyl, imidazolyl, $C_1$-$C_6$alkylcarbonyl-amino or $C_1$-$C_6$alkyloxycarbonylamino;

Het is a heterocyclic group comprising one or two heteroatoms selected from O and N and having 4 to 7 ring atoms wherein said heterocyclic ring is connected to the carbonyl carbon by a ring carbon atom and wherein at least one of said heteroatoms is adjacent to said ring carbon atom, $R^2$ and $R^3$, independently from one another, are hydrogen, hydroxyl, $C_1$-$C_4$alkyl or halo;

$R^4$ and $R^5$, independently from one another, are hydrogen, $C_1$-$C_4$alkyl, halo or methoxy;

each $R^7$ independently is hydrogen, phenyl, or $C_1$-$C_4$ alkyl optionally substituted with methoxy or phenyl; and, $R^8$ is $C_1$-$C_4$alkyl or benzyl;

or a pharmaceutically acceptable salt and/or solvate thereof.

In one embodiment, the present invention provides compounds, which can be represented by the formula I:

(I)

including any possible stereoisomers thereof, wherein:

R and $R^1$, independently from one another, are benzoyl optionally substituted with one, two or three substituents each independently selected from halo and $C_1$-$C_6$alkyl, or —C(=O)-Het, or a group of formula —C(=O)—CH($R^x$)—$R^6$, benzyloxycarbonyl, $C_1$-$C_6$alkyloxycarbonyl, a group of formula $H_2N$—CH($R^7$)—C(=O)—, or a group of formula $R^8$—O—C(=O)—HN—CH($R^7$)—C(=O)—;

$R^6$ is $C_1$-$C_4$alkyl or phenyl wherein the phenyl may be optionally substituted with one, two or three substituents each independently selected from halo and $C_1$-$C_6$alkyl;

$R^x$ is selected from hydrogen, hydroxy, $C_1$-$C_6$alkoxy, amino, mono- or di$C_1$-$C_6$alkyl-amino, pyrrolidinyl, piperidinyl, morpholinyl, $C_1$-$C_6$alkylcarbonylamino or $C_1$-$C_6$alkyloxycarbonylamino;

Het is a heterocyclic group comprising one or two heteroatoms selected from O and N and having 4 to 7 ring atoms wherein said heterocyclic ring is connected to the carbonyl carbon by a ring carbon atom and wherein at least one of said heteroatoms is adjacent to said ring carbon atom, $R^2$ and $R^3$, independently from one another, are hydrogen, hydroxyl, $C_1$-$C_4$alkyl or halo;

$R^4$ and $R^5$, independently from one another, are hydrogen, $C_1$-$C_4$alkyl, halo or methoxy;

each $R^7$ independently is hydrogen, $C_1$-$C_4$ alkyl, or phenyl; and, $R^8$ is $C_1$-$C_4$alkyl or benzyl; or a pharmaceutically acceptable salt and/or solvate thereof.

In a further aspect, the invention concerns the use of compounds of formula I, as specified herein, for inhibiting HCV. Alternatively, there is provided the use for the manufacture of a medicament of a compound of formula I, as specified herein.

Embodiments of the present invention concerns compounds of formula (I), or any subgroup thereof as defined herein, wherein one or more of the definitions for R, $R^1$, $R^2$, $R^3$, $R^4$, $R^5$, $R^6$, $R^7$, $R^8$, $R^x$ and/or Het as specified herein, apply.

Subgroups of compounds of formula I are those compounds of formula I, or subgroups of compounds of formula I, as defined herein, wherein R and $R^1$ are benzylcarbonyl or isobutyloxycarbonyl, in particular wherein R and $R^1$ are benzylcarbonyl.

Subgroups of compounds of formula I are those compounds of formula I, or subgroups of compounds of formula I, as defined herein, wherein R and $R^1$, independently from one another, may be a group of formula —C(=O)—CH($R^x$)—$R^6$ or —C(=O)-Het, in particular wherein R and $R^1$, independently from one another, are groups of formula —C(=O)—CH($R^x$)—$R^6$.

Subgroups of compounds of formula I are those compounds of formula I, or subgroups of compounds of formula I, as defined herein, wherein $R^x$ is hydroxy, $C_1$-$C_6$alkoxy, amino, mono- or di$C_1$-$C_6$alkylamino, pyrrolidinyl, piperidinyl, morpholinyl, $C_1$-$C_6$alkylcarbonylamino or $C_1$-$C_6$alkyloxycarbonylamino; or wherein $R^x$ is hydroxyl, amino, di$C_1$-$C_4$alkylamino, or morpholinyl; or wherein $R^x$ is hydroxy, amino or dimethylamino.

Subgroups of compounds of formula I are those compounds of formula I, or subgroups of compounds of formula I, as defined herein, wherein $R^6$ is a phenyl ring optionally substituted with one halo or $C_1$-$C_6$alkyl; or wherein the phenyl ring is unsubstituted. Alternatively, $R^6$ is selected from phenyl and isopropyl.

Subgroups of compounds of formula I are those compounds of formula I, or subgroups of compounds of formula I, as defined herein, wherein Het as defined above has 4, 5 or 6 ring atoms; or wherein Het is selected from 2-pyridinyl, 2-pyrimidyl, 2-pyrazinyl, 2-imidazoyl, 2-thiazolyl, 2-thiophenyl, 2-pyrazolinyl, 2-piperidinyl, 2-pyrrolidinyl, 2-pyrrolyl, 2-furanyl, 2-tetrahydrofuranyl, 2-oxetanyl, 2- or 3-morpholinyl, and 2-piperazinyl, in particular 2-tetrahydrofuranyl.

Subgroups of compounds of formula I are those compounds of formula I, or subgroups of compounds of formula I, as defined herein, wherein $R^2$ and $R^3$ are independently hydrogen, hydroxy or fluoro, in particular wherein $R^2$ and $R^3$ are hydrogen.

Subgroups of compounds of formula I are those compounds of formula I, or subgroups of compounds of formula I, as defined herein, wherein $R^4$ and $R^5$ are independently hydrogen, methyl, methoxy or chloro, in particular wherein $R^4$ and $R^5$ are hydrogen.

Subgroups of compounds of formula I are those compounds of formula I, or subgroups of compounds of formula I, as defined herein, wherein $R^8$ is methyl.

Subgroups of compounds of formula I are those compounds of formula I, or subgroups of compounds of formula I, as defined herein, wherein the group

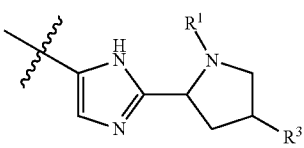

is substituted in meta or para position, relative to the oxygen bridge between the two phenyl groups, in particular, compounds of formula I, as defined herein or subgroups thereof, wherein said group is in meta.

Subgroups of compounds of formula I are those compounds of formula I, or subgroups of compounds of formula I, as defined herein, wherein the group —HN—CH($R^7$)—C(=O)— as part of formula $H_2N$—CH($R^7$)—C(=O)— or formula $R^8$—O—C(=O)—HN—CH($R^7$)—C(=O)—, forms an amino acid residue selected from valine (Val), leucine (Leu), phenylalanine (Phe), MeO-Threonine or phenylglycine. Of particular interest are the L-amino acid residues such as L-Val, L-Leu, L-Phe and L-MeO-Threonine.

Subgroups of compounds of formula I are those compounds of formula I, or subgroups of compounds of formula I, as defined herein, having structural formula Y

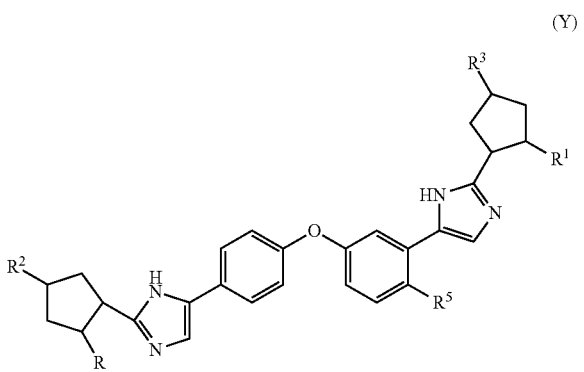

(Y)

wherein R, $R^1$, $R^2$, $R^3$, $R^5$, $R^6$, $R^7$, $R^8$, $R^x$ and/or Het as specified herein, apply In a further aspect, the invention provides a compound of formula I or a pharmaceutically acceptable salt, hydrate, or solvate thereof, for use in the treatment or prophylaxis (or the manufacture of a medicament for the treatment or prophylaxis) of HCV infection. Representative HCV genotypes in the context of treatment or prophylaxis in accordance with the invention include genotype 1b (prevalent in Europe) or 1a (prevalent in North America). The invention also provides a method for the treatment or prophylaxis of HCV infection, in particular of the genotype 1a or 1b.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms or stereoisomers of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereoisomeric forms of the appropriate starting materials, provided that the reaction occurs stereospecifically. Preferably, if a specific stereoisomer is desired, said compound is synthesized by stereospecific methods of preparation. These methods will advantageously employ enantiomerically pure starting materials.

The diastereomeric racemates of the compounds of formula I can be obtained separately by conventional methods. Appropriate physical separation methods that may advantageously be employed are, for example, selective crystallization and chromatography, e.g. column chromatography or supercritical fluid chromatography.

The compounds of formula I have several centers of chirality. Of interest are the stereogenic centers of the pyrrolidine ring at the 2-carbon atom. The configuration at this position may be that corresponding to L-proline, i.e.

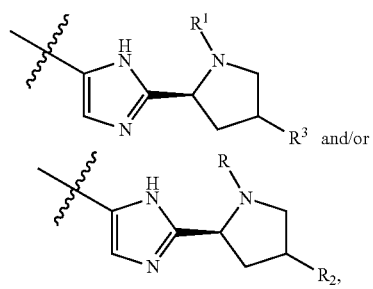

or that corresponding to D-proline, i.e.

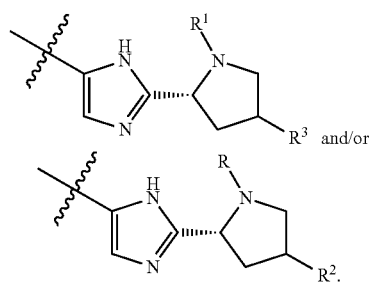

Also of interest are is the stereochemistry at the carbon atom substituted by $R^x$ and $R^6$ in groups of formula —C(=O)—CH($R^x$)—$R^6$, and/or of amino acid residues as defined by formula $H_2N$—CH($R^7$)—C(=O)— or formula $R^8$—O—C(=O)—HN—CH($R^7$)—C(=O)—.

The pharmaceutically acceptable addition salts comprise the therapeutically active non-toxic acid and base addition salt forms of the compounds of formula (I) or subgroups thereof. Of interest are the free, i.e. non-salt forms of the compounds of formula I, or of any subgroup of compounds of formula I specified herein.

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propionic, hydroxyacetic, lactic, pyruvic, oxalic (i.e. ethanedioic), malonic, succinic (i.e. butanedioic acid), maleic, fumaric, malic (i.e. hydroxyl-butanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of formula (I) containing an acidic proton may also be converted into their base addition salts, in particular metal or amine addition salt forms, by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "solvates" covers any pharmaceutically acceptable solvates that the compounds of formula I as well as the salts thereof, are able to form. Such solvates are for example hydrates, alcoholates, e.g. ethanolates, propanolates, and the like.

Some of the compounds of formula I may also exist in tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

As used herein, "$C_1$-$C_4$alkyl" as a group or part of a group defines saturated straight or branched chain hydrocarbon groups having from 1 to 4 carbon atoms such as for example methyl, ethyl, 1-propyl, 2-propyl, 1-butyl, 2-butyl, 2-methyl-1-propyl, 2-methyl-2-propyl. "$C_1$-$C_6$alkyl" encompasses $C_1$-$C_4$alkyl groups and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_1$-$C_6$alkyl is $C_1$-$C_4$alkyl.

"$C_1$-$C_6$alkoxy" or "$C_1$-$C_6$alkyloxy" means a group of formula —O—$C_1$-$C_6$alkyl wherein $C_1$-$C_6$alkyl is as defined above. Examples of $C_1$-$C_6$alkoxy are methoxy, ethoxy, n-propoxy, or isopropoxy. Of interest amongst $C_1$-$C_6$alkoxy are $C_1$-$C_4$alkoxy, i.e. a group of formula —O—$C_1$-$C_4$alkyl wherein $C_1$-$C_4$alkyl is as defined above.

The term "$C_3$-$C_6$cycloalkyl" is generic to cyclopropyl, cyclobutyl, cyclopentyl and cyclohexyl.

The term "halo" is generic to fluoro, chloro, bromo and iodo.

As used herein, the term "(=O)" or "oxo" forms a carbonyl moiety when attached to a carbon atom. It should be noted that an atom can only be substituted with an oxo group when the valency of that atom so permits.

As used herein for the purpose of defining Het, a heterocyclic group may comprise one or two heteroatoms selected from O and N and have 4, 5, 6 or 7 ring atoms.

Where the position of a group on a molecular moiety is not specified (for example a substituent on phenyl) or is represented by a floating bond, such group may be positioned on any atom of such a moiety, as long as the resulting structure is chemically stable. When any variable is present more than once in the molecule, each definition is independent.

Whenever used herein, the term "compounds of formula I", or "the present compounds" or similar terms, it is meant to include the compounds of formula I, including the possible stereoisomeric forms, and the pharmaceutically acceptable salts and solvates thereof.

General Synthetic Methods

The compounds of formula (I) wherein R and $R^1$ have the same meanings, said compounds being represented by formula (Ia), can be prepared by reacting a bis-pyrrolidinyl derivative of formula (II) with an intermediate R—W or $R^1$—W in an amide or carbamate forming reaction as illustrated by Scheme 1. For amide formation W is hydroxy or a activating group and for carbamate formation W is an activating group. Activating groups are halides, in particular chlorides, mixed anhydrides or active esters.

Scheme 1

In the above and the following reaction schemes, the α-carbon atom in the pyrrolidine rings can be racemic or can have one of the stereochemical configurations (R or S).

The amide forming reaction comprises reacting the starting materials, i.e. a carboxylic acid derivative and bispyrrolidinyl (II), for example phenyl acetic acid, mandelic acid, tolylacetic acid, with an amide-coupling reagent in a reaction-inert solvent, optionally in the presence of a base. Solvents that can be used comprise halogenated hydrocarbons such as dichloromethane (DCM) or chloroform, ethers such as tetrahydrofuran (THF) or 2-methyltetrahydrofuran (MeTHF), hydrocarbon solvents such as toluene or xylene, dipolar aprotic solvents such as DMF, DMA, acetonitrile, or mixtures thereof. Amide-coupling agents comprise agents such as N-ethoxycarbonyl-2-ethoxy-1,2-dihydro-quinoline (EEDQ), N-isopropoxycarbonyl-2-isopropoxy-1,2-dihydro-quinoline, in particular its hydrochloride salt, (IIDQ), N,N,N',N'-tetramethyl-O-(7-azabenzotriazol-1-yl)uronium hexafluorophosphate (HATU), benzotriazol-1-yl-oxy-tris-pyrrolidino-phosphonium hexafluorophosphate (commercially available as PyBOP®), 1,1'-carbonyldiimidazole (CDI), 1-ethyl-3-(3-dimethylaminopropyl) carbodiimide (EDI or EDCI) as well as its hydrochloride salt, dicyclohexyl-carbodiimide (DCC), or 1,3-diisopropylcarbodiimide, O-benzotriazole-N,N,N',N'-tetramethyl-uronium-hexafluoro-phosphate (HBTU) and the like. A catalyst may be added, for example 1-hydroxybenzotriazole (HOBt) or 4-dimethylaminopyridine (DMAP). The reaction is usually conducted in the presence of a base, in particular an amine base such as a tertiary amine, e.g. triethylamine, N-methyl-morpholine, N,N-diisopropylethylamine, (the latter also being referred to as Hünig's base, DIPEA, or DIEA). In one embodiment, the reaction is conducted in DMF with HATU in the presence of N,N-diisopropylethylamine as base.

Amides can also be prepared by reacting an activated acid such as a carboxylic acid halide, in particular chloride, or a mixed anhydride or active ester with (II). In active esters, W is an aryloxy group such as phenoxy, p-nitrophenoxy, pentafluorophenoxy, trichloro-phenoxy, pentachlorophenoxy and the like; or W can be the rest of a mixed anhydride, i.e. W is —O—CO—Z or —O—CO—OZ, Z in the latter being e.g. $C_{1-4}$alkyl, such as methyl, ethyl, propyl, i-propyl, butyl, t-butyl, i-butyl, or Z is benzyl).

Carbamate forming reactions may be conducted using a variety of methods, in particular by reaction of the bispyrrolidinyl derivative of formula (II) with alkyl chloroformates; although not preferred, by reaction of alcohols with carbamoyl chlorides or isocyanates; via reactions involving metal complexes or acyl transfer agents. Carbon monoxide and certain metal catalysts can also be used to synthesize carbamates. Metals such as palladium, iridium, uranium, and platinum may be used as catalysts.

One approach for the preparation of carbamates involves the use of intermediates of formula R'—O—CO-Q, wherein R' is $C_1$-$C_6$alkyl or benzyl and Q is leaving group such as halo, in particular chloro and bromo, or a group used in active esters for amide bond formation, such as those mentioned above. Intermediates R'—O—CO-Q can be derived from alcohols R'—OH and phosgene, thus forming a chloroformate, or by transferring the chloro in the latter to other active groups.

Reactions with activated acids or carbamate forming reactions can be conducted using similar reaction conditions as described above for the reactions with amide-coupling agents.

The bispyrrolidinyl derivatives of formula (II) wherein one of the pyrrolidino imidazolyl groups is in meta position, hereinafter referred to as (II-m) can be prepared as illustrated in the following reaction scheme.

Scheme 2

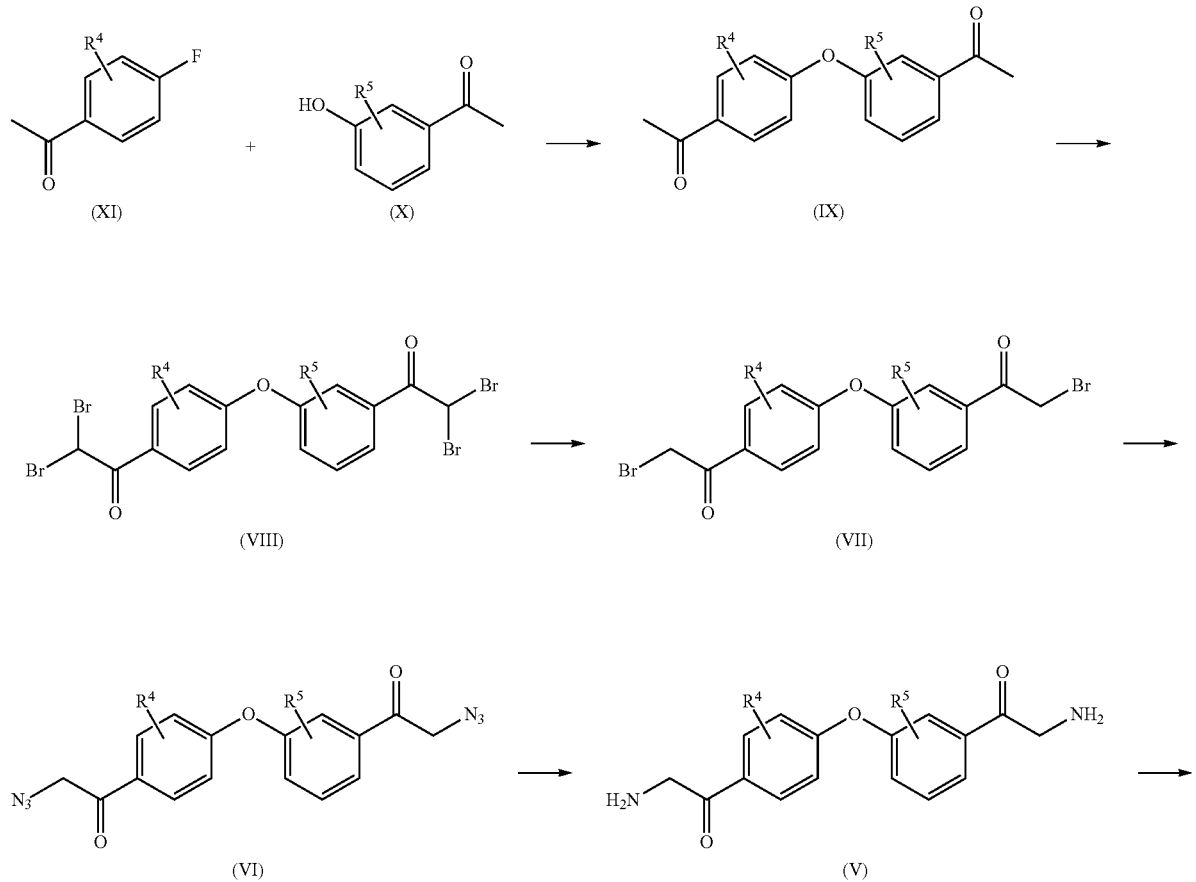

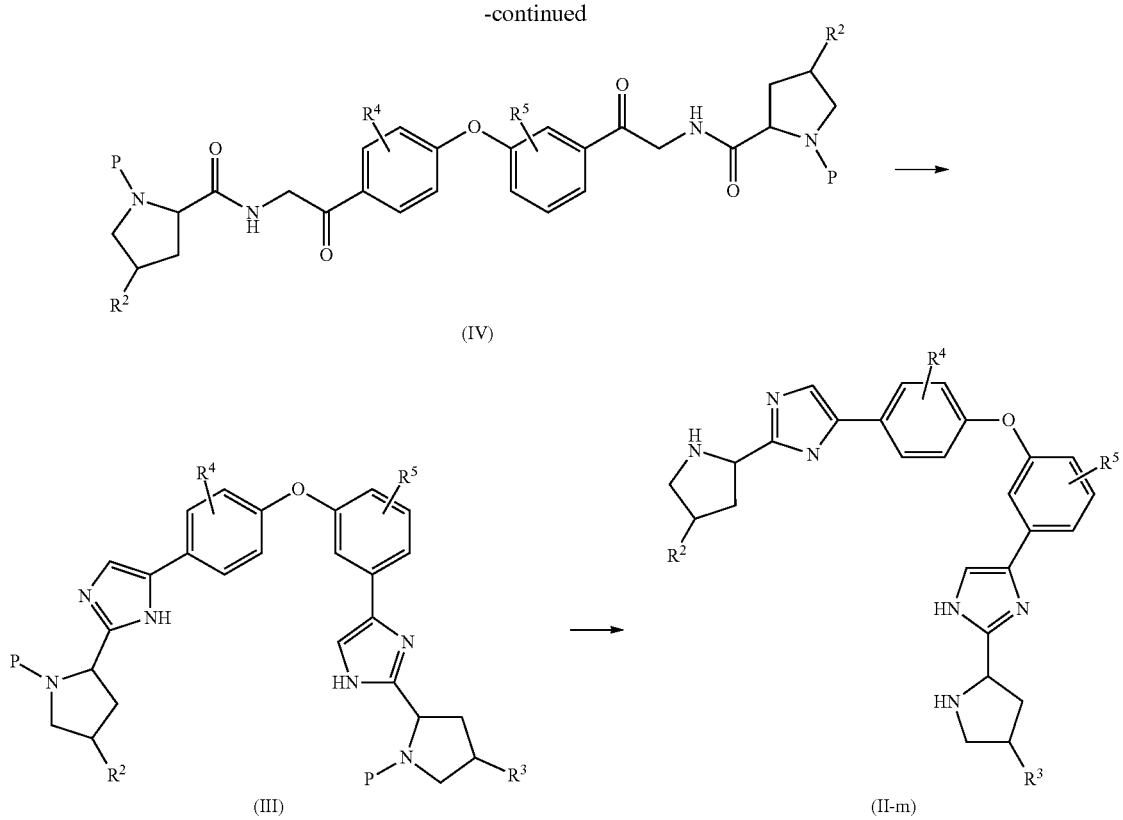

A 1-(3-(4-acetylphenoxy)phenyl)ethanone derivative (IX) can be prepared by forming a bisphenylether group by an aromatic substitution reaction of a 1-(3-hydroxyphenyl)-ethanone derivative (X) on a 1-(4-fluorophenyl)ethanone derivative (XI) in the presence of a base such as potassium carbonate. Said (IX) is brominated with bromine to a 2,2-dibromo-1-(3-(4-(2,2-dibromoacetyl)phenoxy)phenyl)etha-none derivative (VIII). The latter can be converted to a 2-bromo-1-(3-(4-(2-bromoacetyl)phenoxy)-phenyl)etha-none derivative (VII) by reaction with a phosphite, e.g. diethyl phosphite, whereafter the bromo atoms can be substituted with azido groups using an azide salt such as sodium azide. The azido groups in the resulting bisazide compound (VI) can be reduced with hydrogen in the presence of a noble metal catalyst, e.g. hydrogen in the presence of Pd, yielding a 2-amino-1-(3-(4-(2-aminoacetyl)phenoxy)phenyl)ethanone derivative (V). The latter can be coupled with an N-protected proline derivative yielding phenoxyphenyl derivative (IV), wherein P is a amino protecting group, e.g. tert-butyloxycar-bonyl (BOC).

In a next step (IV) is cyclized with ammonium acetate to intermediate (III), wherein P is as specified above. Removal of P, for example where P is BOC by reaction with acid, e.g. with aqueous HCl, yields (II-m). The latter can be used as a starting material to prepare various compounds of formula (I) by introducing acyl or carbamate groups.

Alternatively, compound (VII) can be transformed in compound (III) by similar methods as used in the transformation of compound (XIV) (Scheme 3) to compound (XII), as for example described in example 17.

The bispyrrolidinyl derivatives of formula (II) wherein both pyrrolidino imidazolyl groups are in para position relative to one another, hereinafter referred to as (II-p) can be prepared as illustrated in reaction scheme 3.

Scheme 3

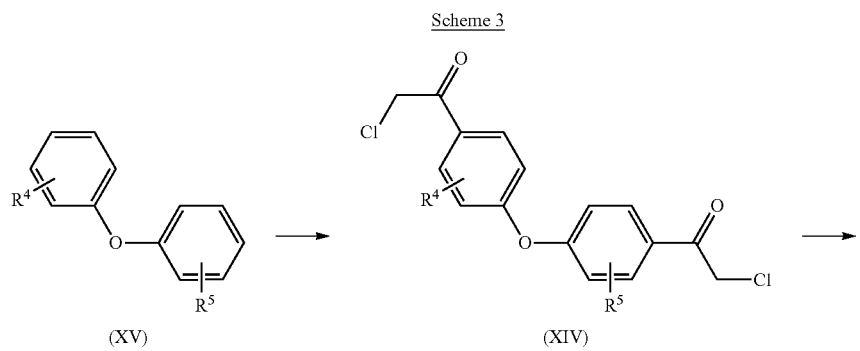

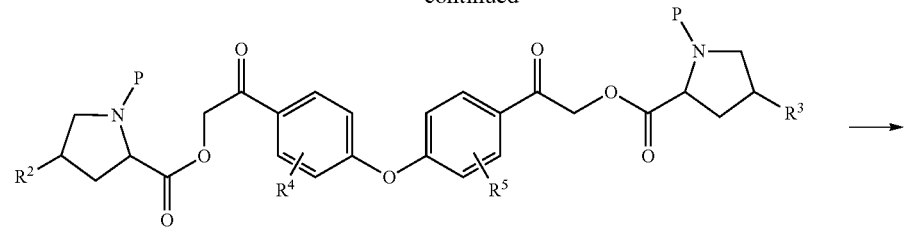

(XIII)

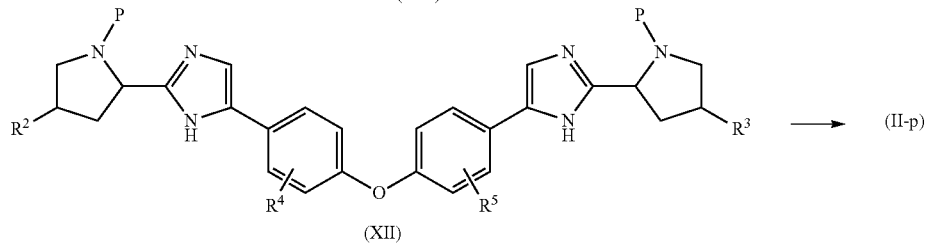

(XII) → (II-p)

A 1,1'-(4,4'-oxybis(4,1-phenylene))bis(2-chloroethanone) derivative (XIV) can be prepared by performing a friedel crafts acylation on a diarylether (XV) in the presence of a Lewis acid such as aluminum chloride and an acid chloride, possibly using carbon disulfide as a solvent, preferably heating to reflux. Acylation with chloroacetyl chloride results in alpha-haloketone (XIV). The resulting halogenated ketone is reacted with an amino acid such as Boc-L-proline to form an ester, using a soluble organic base such as triethylamine or diisopropylethylamine. The ester product (XIII) is then cyclized with ammonium acetate to the intermediate (XII). The cyclisation may be performed in a sealed tube along with an ammonia source in excess, for example ammonium acetate, and heated in a conventional manner or in the microwave, to produce intermediate (XII). Removal of P, for example where P is BOC by deprotection with acid, e.g. with aqueous HCl, yields (II-p).

The compounds of formula (I) wherein R and $R^1$ having different meanings, hereafter represented by formula (I-b), can be prepared as outlined in reaction scheme 4.

Scheme 4

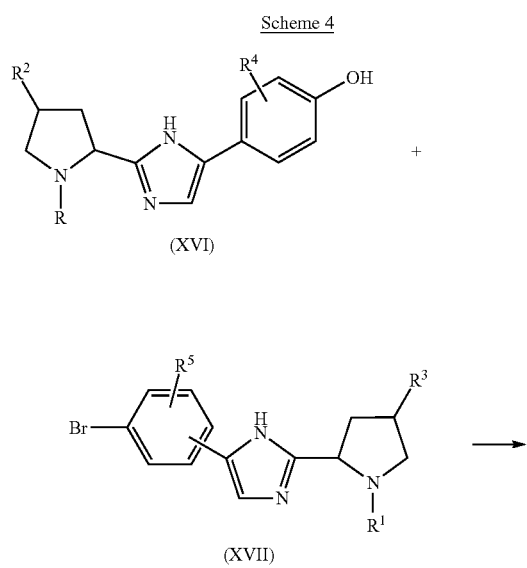

(XVI)

+

(XVII)

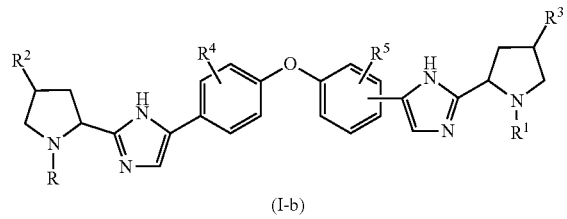

(I-b)

R and $R^1$ in (I-b) are different groups having the meanings defined above.

The reaction of (XVI) with (XVII) is conducted with a transition metal catalyst, in particular a Pd° complex such as palladium tetrakis triphenyl phosphine, or a copper(II) salt such as copper(II)triflate, or with Cu°. The intermediates of formula (XVI) can be prepared from the corresponding protected phenol, e.g. the corresponding methoxy analog, which is demethylated using for example Boron tribromide (BBr$_3$). The corresponding methoxy analog (XVIa) can be prepared as illustrated in Scheme 5. Compound of formula (XVIa) may be obtained starting from compound of formula (XVIII) using the same type of procedures as described herein above for the steps to convert compound (IX) into compound (III).

Scheme 5

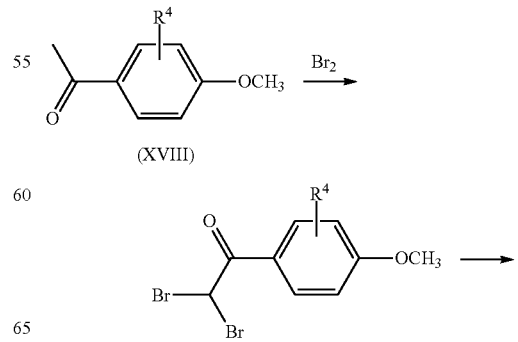

(XVIII)

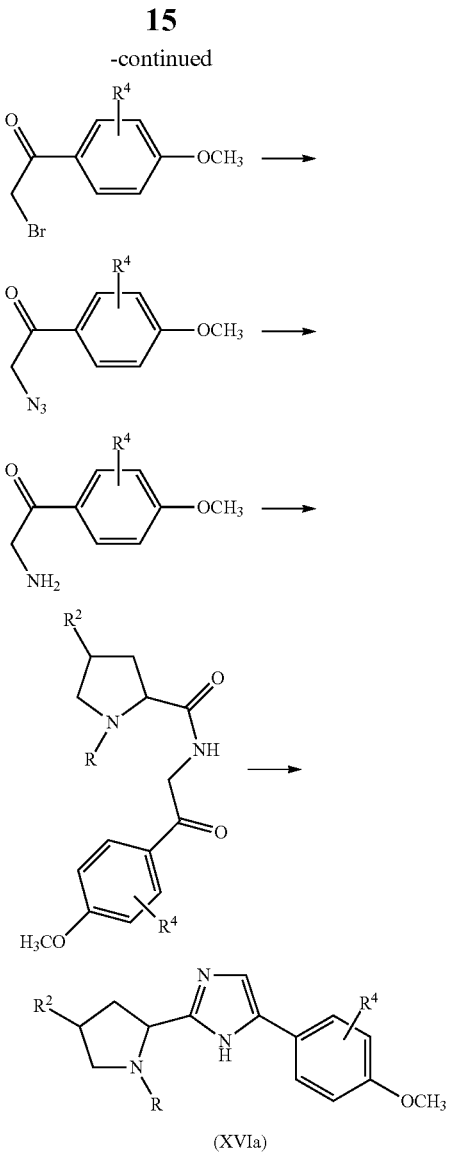

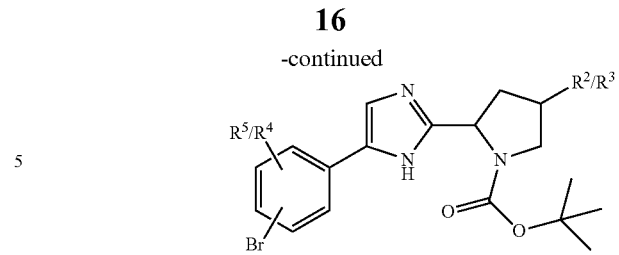

Scheme 6 illustrates that the intermediates (XVII) may be obtained from a bromo,bromoacetyl-phenyl derivative using similar procedures as described in the conversion of compound (XIV) into compound (XII).

Scheme 6

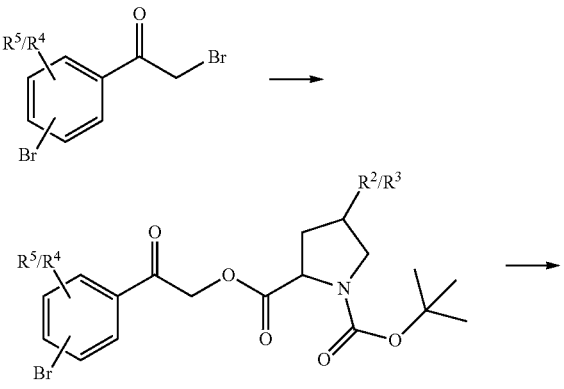

In a further aspect, the present invention concerns a pharmaceutical composition comprising a therapeutically effective amount of a compound of formula I as specified herein, and a pharmaceutically acceptable carrier. A therapeutically effective amount in this context is an amount sufficient to act in a prophylactic way against HCV infection, to stabilize or to reduce HCV infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula I, as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula I show activity against HCV and can be used in the treatment and prophylaxis of HCV infection or diseases associated with HCV. The latter include progressive liver fibrosis, inflammation and necrosis leading to cirrhosis, end-stage liver disease, and HCC. A number of the compounds of this invention moreover are believed to be active against mutated strains of HCV. Additionally, compounds of this invention may show a favorable pharmacokinetic profile and have attractive properties in terms of bioavailability, including an acceptable half-life, AUC (area under the curve) and peak values and lacking unfavorable phenomena such as insufficient quick onset and tissue retention.

The in vitro antiviral activity against HCV of the compounds of formula I can be tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula I, as specified herein, are useful in the inhibition of HCV replication, in particular in the treatment of warm-blooded animals, in particular humans, infected with HCV, and for the prophylaxis of HCV infections. The present invention furthermore relates to a method of treating a warm-blooded animal, in particular human, infected by HCV, or being at risk of infection by HCV, said method comprising the administration of an anti-HCV effective amount of a compound of formula I, as specified herein.

The compounds of formula I, as specified herein, may therefore be used as a medicine, in particular as an anti HCV medicine. Said use as a medicine or method of treatment comprises the systemic administration to HCV infected subjects or to subjects susceptible to HCV infection of an amount effective to combat the conditions associated with HCV infection.

The present invention also relates to the use of the present compounds in the manufacture of a medicament for the treatment or the prevention of HCV infection.

In general it is contemplated that an antiviral effective daily amount would be from about 0.01 to about 50 mg/kg, or about 0.02 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The invention also relates to a combination of a compound of formula I, a pharmaceutically acceptable salt or solvate thereof, and another antiviral compound, in particular another anti-HCV compound. The term "combination" may relate to a product containing (a) a compound of formula I, as specified above, and (b) optionally another anti-HCV compound, as a combined preparation for simultaneous, separate or sequential use in treatment of HCV infections.

The following examples are meant to illustrate the invention and should not be construed as a limitation of its scope.

EXAMPLES SYNTHESIS

Example 1

1-(3-(4-acetylphenoxy)phenyl)ethanone

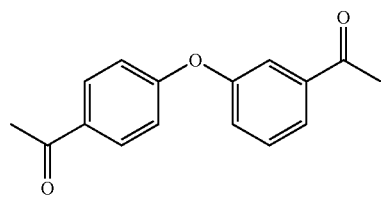 [SMILES: CC(=O)c1ccc(Oc2cccc(C(C)=O)c2)cc1]

A mixture of 1-(3-hydroxyphenyl)ethanone (8 g, 58.7 mmol), 1-(4-fluorophenyl)ethanone (8.1 g, 58.7 mmol) and anhydrous potassium carbonate (16.2 g, 117.5 mmol) in DMSO (150 mL) was stirred for 16 hours at 140° C. The mixture was partitioned between ethyl acetate and water. The aqueous layer was acidified with 1M HCl until pH=6-7 and extracted with ethyl acetate. The combined organics were washed with brine, dried (MgSO$_4$), filtered, and concentrated under reduced pressure. The crude product was chromatographed on silica gel (ethyl actetate/heptane: 1/1) resulting in 1-(3-(4-acetylphenoxy)phenyl)ethanone (11 g, 74%) as a white solid.

LC/MS: m/z=256.2 (M+1)$^+$. Exact mass: 255.1.

Example 2

2,2-dibromo-1-(3-(4-(2,2-dibromoacetyl)phenoxy)phenyl)ethanone

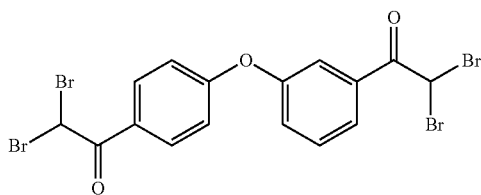 [SMILES: O=C(c1ccc(Oc2cccc(C(=O)C(Br)Br)c2)cc1)C(Br)Br]

To a solution of 1-(3-(4-acetylphenoxy)phenyl)ethanone (11 g, 43.2 mmol) in chloroform (300 mL), bromine (6.6 mL, 129.7 mmol) was added drop wise. The reaction was stirred for 4 hours at 80° C., cooled to room temperature and concentrated under reduced pressure. The mixture was partitioned between ethylacetate and water. The aqueous layer was extracted with ethyl acetate, and the combined organic layers were dried (MgSO$_4$), filtered, and concentrated in vacuo. The resultant crude material was purified by flash chromatography (silica gel: EtOAc/heptane: 3/7) to afford 2,2-dibromo-1-(3-(4-(2,2-dibromoacetyl)phenoxy)phenyl)ethanone as a yellow solid (16 g, 65%).

Example 3

2-bromo-1-(3-(4-(2-bromoacetyl)phenoxy)phenyl)ethanone

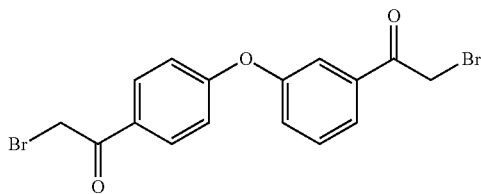 [SMILES: O=C(CBr)c1ccc(Oc2cccc(C(=O)CBr)c2)cc1]

To a solution of 2,2-dibromo-1-(3-(4-(2,2-dibromoacetyl)phenoxy)phenyl)ethanone (16 g, 28 mmol) in tetrahydrofuran (300 mL) at 0° C. was added triethylamine (3.6 mL) and diethyl phosphite (10.7 mL, 83.2 mmol). The reaction was warmed gradually to room temperature and the mixture was stirred during 30 minutes and concentrated under reduced pressure. The mixture was partitioned between ethyl acetate and water. The aqueous layer was extracted with EtOAc and the combined organic layers were dried (MgSO$_4$), filtered, and concentrated in vacuo. The resultant crude material was purified by flash chromatography (silica gel: EtOAc/heptane: 3/7) to afford 2-bromo-1-(3-(4-(2-bromoacetyl)phenoxy)phenyl)ethanone (10.2 g, 88%) as yellow oil.

Example 3a 2-bromo-1-(4-(3-(2-bromoacetyl)-4-methoxyphenoxy)phenyl)ethanone

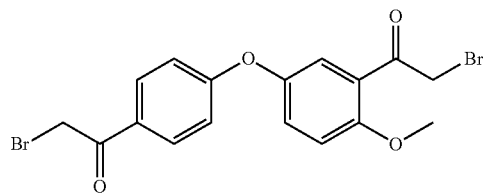 [SMILES: COc1ccc(Oc2ccc(C(=O)CBr)cc2)cc1C(=O)CBr]

2-bromo-1-(4-(3-(2-bromoacetyl)-4-methoxyphenoxy)phenyl)ethanone was synthesized using similar procedure as described in example 1 to 3 with 1-(5-hydroxy-2-methoxyphenyl)ethanone and 1-(4-fluorophenyl)ethanone as starting material.

Example 4

2-azido-1-(3-(4-(2-azidoacetyl)phenoxy)phenyl)ethanone

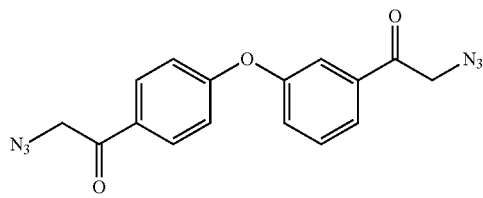 [SMILES: [N-]=[N+]=NCC(=O)c1ccc(Oc2cccc(C(=O)CN=[N+]=[N-])c2)cc1]

To a solution of 2-bromo-1-(3-(4-(2-bromoacetyl)phenoxy)phenyl)ethanone (10.2 g, 24.3 mmol) in DMSO (200 mL) was added sodium azide (3.5 g, 53.4 mmol). The reaction mixture was stirred during 60 minutes at room temperature and then concentrated under reduced pressure. The crude mixture was partitioned between ethyl acetate and water. The aqueous layer was extracted with ethyl acetate and the combined organic layers were dried (MgSO$_4$), filtered, and concentrated in vacuo. The crude product was used as such in the next step.

Example 5

2-amino-1-(3-(4-(2-aminoacetyl)phenoxy)phenyl)ethanone dihydrochloride

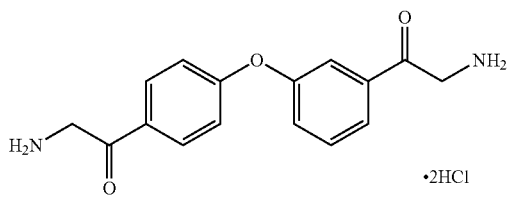 [SMILES: NCC(=O)c1ccc(Oc2cccc(C(=O)CN)c2)cc1]

To a solution of 2-azido-1-(3-(4-(2-azidoacetyl)phenoxy)phenyl)ethanone (9 g, 26.4 mmol) in methanol (400 mL) was added HCl (1M in methanol, 53 mL) and the mixture was hydrogenated using Pd/C (10%) under hydrogen atmosphere (1 bar) during 2 hours. The solution was filtered over celite and concentrated under reduced pressure. The crude was dissolved in dichloromethane and after addition of HCl (6N in isopropanol) the hydrochloride salt precipitated. Filtration and drying in vacuo afforded 2-amino-1-(3-(4-(2-aminoacetyl)phenoxy)phenyl)ethanone dihydrochloride.

LC/MS: m/z=285.2 (M+1)$^+$. Exact mass: 284.1

Example 6

(S)-tert-butyl 2-(2-(3-(4-(2-((S)-1-(tert-butoxycarbonyl)pyrrolidine-2-carboxamido)acetyl)phenoxy)phenyl)-2-oxoethylcarbamoyl)pyrrolidine-1-carboxylate

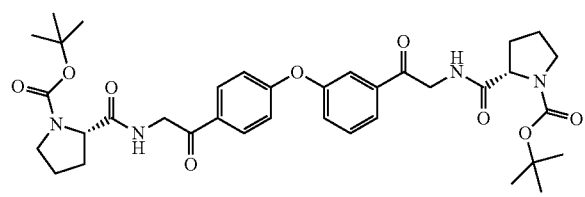 [SMILES: CC(C)(C)OC(=O)N1CCC[C@H]1C(=O)NCC(=O)c1ccc(Oc2cccc(C(=O)CNC(=O)[C@@H]3CCCN3C(=O)OC(C)(C)C)c2)cc1]

To a solution of 2-amino-1-(3-(4-(2-aminoacetyl)phenoxy)phenyl)ethanone dihydrochloride (5.65 g, 15.8 mmol) in DMF (200 mL) was added N,N-diisopropyl-ethylamine (10.4 mL), HATU (15 g, 39.54 mmol) and BOC-L-proline (7.5 g, 34.7 mmol). The mixture was stirred at room temperature during 60 minutes and then concentrated under reduced pressure. The mixture was partitioned between EtOAc and water. The aqueous layer was extracted with EtOAc and the combined organic layers were dried (MgSO$_4$), filtered, and concentrated in vacuo. The resultant crude material was purified by flash chromatography (silica gel: dichloromethane/MeOH: 9/1) to afford (S)-tert-butyl 2-(2-(3-(4-(2-((S)-1-(tert-butoxycarbonyl)pyrrolidine-2-carboxamido)acetyl)phenoxy)phenyl)-2-oxoethylcarbamoyl)pyrrolidine-1-carboxylate as yellow oil (8 g, 74.5%).

LC/MS:: m/z=679.3 (M+1)$^+$. Exact mass: 678.3

Example 7

(S)-tert-butyl 2-(5-(4-(3-(2-((S)-1-(tert-butoxycarbonyl)pyrrolidin-2-yl)-1H-imidazol-4-yl)phenoxy)phenyl)-1H-imidazol-2-yl)pyrrolidine-1-carboxylate

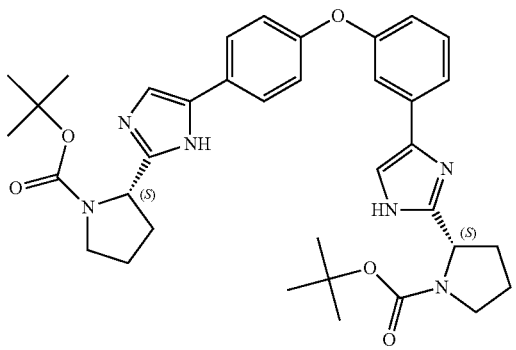

To a solution of (S)-tert-butyl 2-(5-(4-(3-(2-((S)-1-(tert-butoxycarbonyl)pyrrolidin-2-yl)-1H-imidazol-4-yl)phenoxy)phenyl)-1H-imidazol-2-yl)pyrrolidine-1-carboxylate (1.3 g, 17.6 mmol) in p-xylene (20 mL) was added HOAc (0.5 mL) and ammonium acetate (600 mg, 0.88 mmol) in a sealed tube. The mixture was heated in the microwave during two hours at 140° C. The mixture was partitioned between EtOAc and water. The aqueous layer was extracted with EtOAc and the combined organics layers were dried (MgSO$_4$), filtered, and concentrated in vacuo. The resultant crude material was purified by flash chromatography (silica gel: dichloromethane/MeOH: 9/1) to afford (S)-tert-butyl 2-(5-(4-(3-(2-((S)-1-(tert-butoxycarbonyl)pyrrolidin-2-yl)-1H-imidazol-4-yl)phenoxy)phenyl)-1H-imidazol-2-yl)pyrrolidine-1-carboxylate (420 mg, 74%).

LC/MS: m/z=641.2 (M+1)$^+$. Exact mass: 640.3

Example 8

2-((S)-pyrrolidin-2-yl)-5-(4-(3-(2-((S)-pyrrolidin-2-yl)-1H-imidazol-4-yl)-phenoxy)phenyl)-1H-imidazole hydrochloride

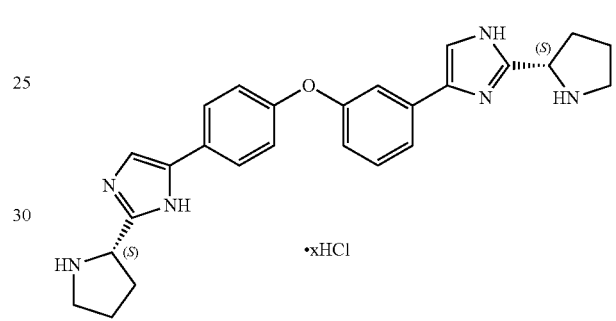

To a solution of (S)-tert-butyl 2-(5-(4-(3-(2-((S)-1-(tert-butoxycarbonyl)pyrrolidin-2-yl)-1H-imidazol-4-yl)phenoxy)phenyl)-1H-imidazol-2-yl)pyrrolidine-1-carboxylate (500 mg, 0.78 mmol) in dichloromethane was added HCl (1 M, 3 mL), the reaction product precipitated after stirring at room temperature. Filtration and drying in the vacuum oven afforded 2-((S)-pyrrolidin-2-yl)-5-(4-(3-(2-((S)-pyrrolidin-2-yl)-1H-imidazol-4-yl)phenoxy)phenyl)-1H-imidazole hydrochloride (220 mg).

Example 9

2-phenyl-1-((S)-2-(5-(4-(3-(2-((S)-1-(2-phenylacetyl)pyrrolidin-2-yl)-1H-imidazol-4-yl)phenoxy)phenyl)-1H-imidazol-2-yl)pyrrolidin-1-yl)ethanone

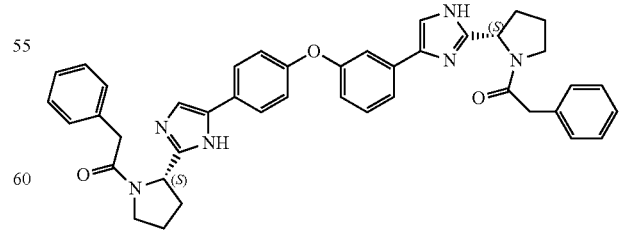

To a solution of 2-((S)-pyrrolidin-2-yl)-5-(4-(3-(2-((S)-pyrrolidin-2-yl)-1H-imidazol-4-yl)phenoxy)phenyl)-1H-imidazole hydrochloride (72 mg) in DMF (20 mL) was added was added N,N-diisopropylethylamine (0.1 mL), HATU (155 mg, 0.4 mmol) and phenyl acetic acid (49 mg, 0.36 mmol). The reaction was stirred for 1 hour at room temperature and concentrated under reduced pressure. The crude product was purified by reverse-phase preparative HPLC to provide 2-phenyl-1-((S)-2-(5-(4-(3-(2-((S)-1-(2-phenylacetyl)pyrrolidin-2-yl)-1H-imidazol-4-yl)phenoxy)phenyl)-1H-imidazol-2-yl)pyrrolidin-1-yl)ethanone (6 mg).

LC/MS: m/z=677.6 (M+1)⁺. Exact mass: 676.3

Example 10

2-hydroxy-1-((2S)-2-(5-(4-(3-(2-((2S)-1-(2-hydroxy-2-phenylacetyl)-pyrrolidin-2-yl)-1H-imidazol-4-yl)phenoxy)phenyl)-1H-imidazol-2-yl)pyrrolidin-1-yl)-2-phenylethanone

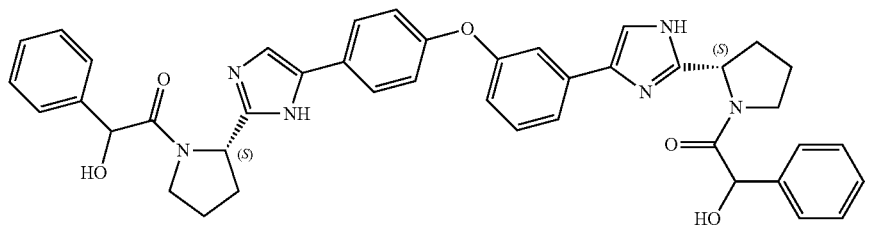

To a solution of 2-((S)-pyrrolidin-2-yl)-5-(4-(3-(2-((S)-pyrrolidin-2-yl)-1H-imidazol-4-yl)phenoxy)phenyl)-1H-imidazole hydrochloride (56 mg) in DMF (15 mL) was added N,N-diisopropylethylamine (0.1 mL), HATU (103 mg, 0.27 mmol) and DL-mandalic acid (36 mg, 0.24 mmol). The reaction was stirred for 1 hour at room temperature and concentrated under reduced pressure. The crude product was purified by reverse-phase preparative HPLC to provide 2-hydroxy-1-((2S)-2-(5-(4-(3-(2-((2S)-1-(2-hydroxy-2-phenylacetyl)pyrrolidin-2-yl)-1H-imidazol-4-yl)phenoxy)phenyl)-1H-imidazol-2-yl)pyrrolidin-1-yl)-2-phenylethanone (3 mg).

LC/MS: m/z=709.4 (M+1)⁺. Exact mass: 708.3

Example 11

2-m-tolyl-1-((2S)-2-(5-(4-(3-(2-((S)-1-(2-m-tolylacetyl)pyrrolidin-2-yl)-1H-imidazol-4-yl)phenoxy)phenyl)-1H-imidazol-2-yl)pyrrolidin-1-yl)ethanone

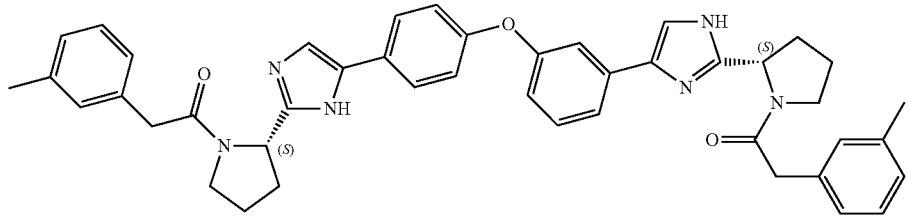

To a solution of 2-((S)-pyrrolidin-2-yl)-5-(4-(3-(2-((S)-pyrrolidin-2-yl)-1H-imidazol-4-yl)phenoxy)phenyl)-1H-imidazole hydrochloride (100 mg, 0.22 mmol) in DMF (22 mL) was added N,N-diisopropylethylamine (0.2 mL), HATU (216 mg, 0.56 mmol) and 2-m-tolyl acetic acid (75 mg, 0.5 mmol). The reaction was stirred for 1 hour at room temperature and concentrated under reduced pressure. The crude product was purified by reverse-phase preparative HPLC to provide 2-m-tolyl-1-((2S)-2-(5-(4-(3-(2-((S)-1-(2-m-tolylacetyl)pyrrolidin-2-yl)-1H-imidazol-4-yl)phenoxy)phenyl)-1H-imidazol-2-yl)pyrrolidin-1-yl)ethanone (5 mg).
LC/MS: m/z=705.2 (M+1)+. Exact mass: 704.3

Example 12

1,1'-(4,4'-oxybis(4,1-phenylene))bis(2-chloroethanone)

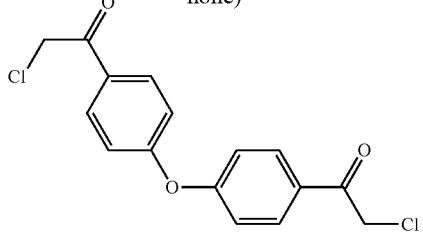

Into a 3-neck round bottom flask equipped with a reflux condensor, and a large magnetic stir bar was placed di-phenyl ether (30 g, 0.176 mol), chloroacetyl chloride (79.6 g, 0.71 mol), and carbondisulfide (100 mL). The mixture is allowed to stir vigorously while Aluminium Chloride (141 g, 1.06 mol) was added in approximately 3 g installments or until the reaction mixture began to boil. When addition was complete the reaction mixture was heated to 100° C. for 2.5 hours with stirring. The reaction was cooled to room temperature and allowed to sit one hour. The top layer (carbon disulfide) was discarded. The bottom layer was divided equally over 4 beakers (1 L each) each containing ice (600 mL) and concentrated hydrochloric acid (50 mL) while stirring vigorously. The mixtures were pooled, and extracted with dichloromethane (5×400 mL). The organic layers were combined, dried over anhydrous sodium sulfate, filtered, and the solvents of the filtrate were removed under reduced pressure to afford a brown oil. The crude mixture was partially purified by flash chromatography using a heptane to ethylacetate gradient. The best fractions were pooled and the solvent removed under reduced pressure to afford a brown oil. The oil is recrystallized in ethylacetate to afford the title product (16.25 g). A second crop afforded a further 25 g.
LC/MS m/z=323 (M+1)+. Exact mass: 322.0
1H-NMR (chloroform-d, 400 MHz): 8.01 ppm (d, 4H), 7.15 ppm (d, 4H), 4.69 ppm (s, 4H).

Example 13

(2S,2'S)-1-tert-butyl '2,2-2,2'-(4,4'-oxybis(4,1-phenylene))bis(2-oxo-ethane-2,1-diyl)dipyrrolidine-1,2-dicarboxylate

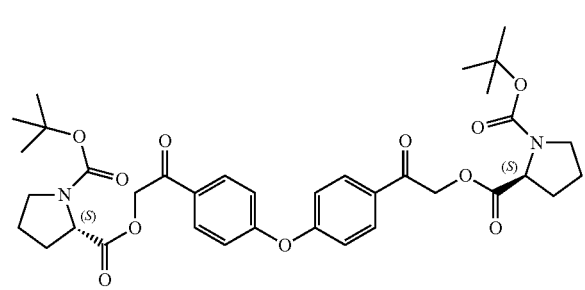

To the compound obtained in example 12 (5 g, 15.5 mmol) in acetonitrile, was added Boc-L-proline (6.99 g, 32.5 mmol), followed by dropwise addition of DIEA (4.4 g, 34.04 mmol). The reaction mixture was stirred for 3 hours at room temperature. The solvents were removed under reduced pressure. Water (50 mL) was added and the mixture was extracted with dichloromethane (3×150 mL). The organic layers were combined, dried (sodium sulfate), filtered, and the solvents of the filtrate removed under reduced pressure. The crude product was purified by flash chromatography using a heptane to ethylacetate gradient to afford the title product.
LC/MS: m/z=681 (M+1)+. Exact mass: 680.3

Example 14

(2S,2'S)-tert-butyl 2,2'-(5,5'-(4,4'-oxybis(4,1-phenylene))bis(1H-imidazole-5,2-diyl))dipyrrolidine-1-carboxylate

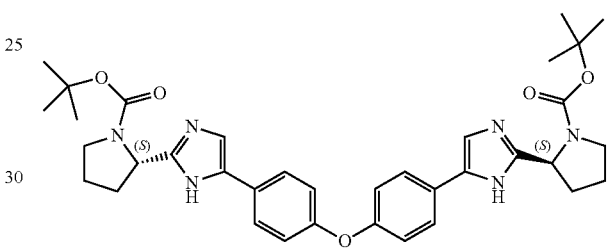

Into a sealable vessel was placed the starting ester obtained in example 13, ammonium acetate (20 eq), and xylene. The mixture was allowed to stir at reflux for several hours to afford the title product. The mixture was partitioned between EtOAc and water. The aqueous layer was extracted with EtOAc and the combined organics layers were dried (MgSO4), filtered, and concentrated in vacuo. The resultant crude material was purified by flash chromatography (silica gel: dichloromethane/MeOH: 9/1) to afford the title product.
LC/MS: m/z=641 (M+1)+. Exact mass: 640.3

Example 15

(S)-5,5'-(4,4'-oxybis(4,1-phenylene))bis(2-((S)-pyrrolidin-2-yl)-1H-imidazole)

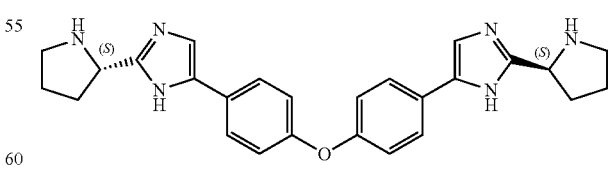

The protecting groups on the proline moieties of the compound obtained in example 14 are removed following the same procedure as described in Example 8.

LC/MS: m/z=441 (M+1)+. Exact mass: 440.2

Furthermore, the deprotected nitrogens of the proline moieties are acylated using the same procedure as in Example 9.

Example 16

(S)-tert-butyl 2-(4-(4-(3-(2-((S)-1-(tert-butoxycarbonyl)pyrrolidin-2-yl)-1H-imidazol-4-yl)-4-methoxyphenoxy)phenyl)-1H-imidazol-2-yl)pyrrolidine-1-carboxylate

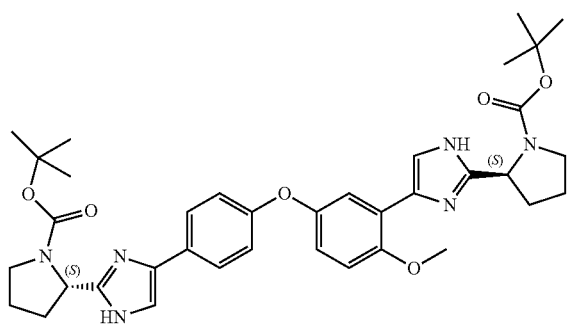

To a solution of 2-bromo-1-(4-(3-(2-bromoacetyl)-4-methoxyphenoxy)phenyl)-ethanone (Example 3a) (10 g, 14 mmol) in acetonitrile (150 mL) was added N-(tert-Butoxycarbonyl)-L-proline (11.2 g, 28 mmol) at room temperature. To this solution, Hunigs base (23 mL, 42 mmol) was added drop wise, after which the mixture was stirred for 6 hours at room temperature. The reaction mixture was then concentrated in vacuo and the crude was diluted with dichloromethane (300 mL). The organic mixture was then washed with water (2×300 mL). The combined organics were dried with magnesiumsulfate. After filtration and evaporation of the solvent, the mixture was purified by flash chromatography (EtOAc/Heptane: 3/7) to give the pure (S)-2-(2-(4-(3-(2-((S)-1-(tert-butoxycarbonyl)pyrrolidine-2-carbonyloxy)acetyl)-4-methoxy-phenoxy)phenyl)-2-oxoethyl) 1-tert-butyl pyrrolidine-1,2-dicarboxylate which was used as such into the next step. (S)-2-(2-(4-(3-(2-((S)-1-(tertbutoxycarbonyl)-pyrrolidine-2-carbonyloxy)acetyl)-4-methoxyphenoxy)phenyl)-2-oxoethyl) 1-tert-butyl pyrrolidine-1,2-dicarboxylate was then dissolved in xylene (150 mL) and NH$_4$OAc (5 eq.) was added. The reaction mixture was stirred for 6 hours at 140° C. Then the mixture was extracted with dichloromethane, the combined organic layers were washed with water and dried over Na$_2$SO$_4$. The mixture was filtrated, the solvent was removed and the residue was purified by flash chromatography (Chloroform/MeOH: 95/5) to afford the title compound (4.1 g, yield: 44%).

$^1$H NMR (400 MHz, CHLOROFORM-d) δ ppm 1.48 (s, 9 H) 1.50 (s, 9 H) 1.86-2.02 (m, 2 H) 2.07-2.23 (m, 4 H) 2.91-3.04 (m, 2 H) 3.39 (br. s., 4 H) 3.97 (br. s., 3 H) 4.97 (dd, J=7.5, 2.4 Hz, 2 H) 6.90 (m, 5 H) 6.98 (d, J=8.6 Hz, 2 H) 7.14 (s, 2 H)

Example 17

Alternative preparation of (S)-tert-butyl 2-(5-(3-(4-(2-((S)-1-(tert-butoxycarbonyl)pyrrolidin-2-yl)-1H-imidazol-4-yl)phenoxy)phenyl)-1H-imidazol-2-yl)pyrrolidine-1-carboxylate

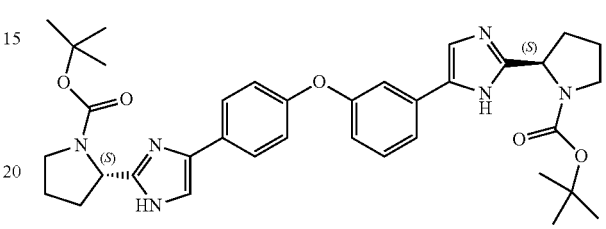

To a solution of 2-bromo-1-(3-(4-(2-bromoacetyl)phenoxy)phenyl)ethanone (2.05 g, 5 mmol) in CH$_2$Cl$_2$ (40 mL) was added N-(tert-Butoxycarbonyl)-L-proline (2.15 g, 10 mmol) at 0° C. Triethylamine (1.0 g, 10 mmol) was then carefully added dropwise and the mixture was stirred at room temperature for 6 hours. Then CH$_2$Cl$_2$ (150 mL) was added, the mixture was washed with water and dried over Na$_2$SO$_4$. After filtration, the solvent was removed and the obtained residue was purified by flash chromatography (n-hexane/ethyl acetate: 2/1) to afford (S)-2-(2-(3-(4-(2-((S)-1-(tert-butoxycarbonyl)pyrrolidine-2-carbonyloxy)acetyl)phenoxy)phenyl)-2-oxoethyl) 1-tert-butyl pyrrolidine-1,2-dicarboxylate yield 2.11 g (63%). A mixture of (S)-2-(2-(3-(4-(2-((S)-1-(tert-butoxycarbonyl)pyrrolidine-2-carbonyloxy)acetyl)phenoxy)phenyl)-2-oxoethyl) 1-tert-butyl pyrrolidine-1,2-dicarboxylate (6.80 g, 10 mmol) and NH$_4$OAc (7.7 g, 100 mmol) in xylene (150 mL) was stirred for 6 hours at 140° C. Then the mixture was extracted with ethylacetate (300 mL), washed with water and dried over Na$_2$SO$_4$. After filtration, the solvent was removed and the obtained residue purified by flash chromatography (Chloroform/MeOH: 95/5) to afford the title compound (50%).

$^1$H NMR (400 MHz, CHLOROFORM-d) δ ppm 1.49 (m, 18 H) 1.84-2.02 (m, 4 H) 2.15 (br. s., 4 H) 3.41 (m, 4 H) 4.86-5.03 (m, 2 H) 6.87 (d, J=7.0 Hz, 1 H) 7.04 (m, 3 H) 7.17 (m, 3 H) 7.32 (m, 3 H)

Examples 18 to 41

General Procedure

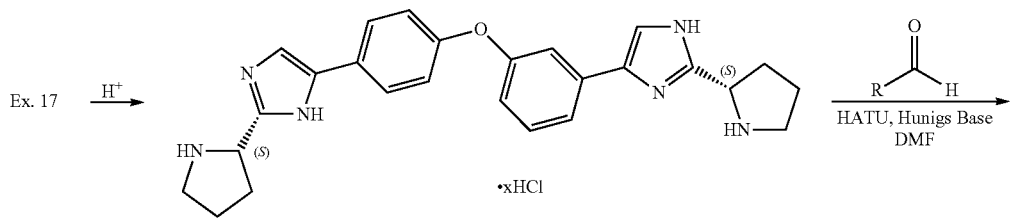

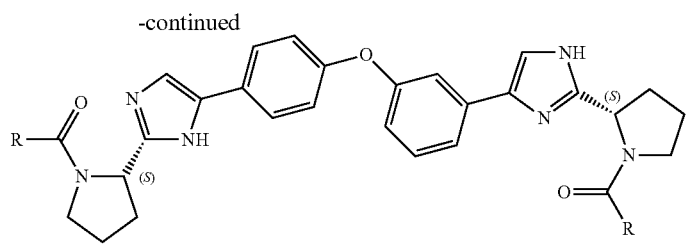

First, to a solution of (S)-tert-butyl 2-(5-(3-(4-(2-((S)-1-(tert-butoxycarbonyl)pyrrolidin-2-yl)-1H-imidazol-4-yl)phenoxy)phenyl)-1H-imidazol-2-yl)pyrrolidine-1-carboxylate in dichloromethane, excess HCl (1M in isopropanol) was added dropwise. The precipitated solid was filtered off and dried in the vacuum oven to afford 2-(pyrrolidin-2-yl)-5-(4-(3-(2-(pyrrolidin-2-yl)-1H-imidazol-4-yl)phenoxy)phenyl)-1H-imidazole hydrochloride.

Subsequently, to a solution of 2-(pyrrolidin-2-yl)-5-(4-(3-(2-(pyrrolidin-2-yl)-1H-imidazol-4-yl)phenoxy)phenyl)-1H-imidazole hydrochloride (300 mg) in DMF (7 ml) was added Hunigs Base (0.45 ml, 2.72 mmol), HATU (647 mg, 1.70 mmol) and corresponding acid (1.5 mmol) The mixture was stirred for 4 hours at room temperature and concentrated in vacuo. The mixture was loaded on a Isolute (SCX-3, 15 mL) plug and the plug was washed with MeOH (4 times). Then, with $NH_3$/MeOH (2 times), the product was rinsed off. The obtained solution was then concentrated in vacuo and the crude product was treated with HCl (1 M in water) and DCM (3/1) until a solid was obtained. The solid was then filtered off, and washed with aqueous HCl (1 M). The product was dried in a vacuum oven to give the target product.

Compounds synthesized in accordance with this general procedure are listed in Table 1. As indicated in Table 1, some compounds were prepared as HCl salts while others were prepared as a free base. Compounds 39, 40, 43 and 44 were further purified by conventional silica gel chromatography (MeOH (7 N $NH_3$)/DCM: 2/98) or reverse phase chromatography.

TABLE 1

18

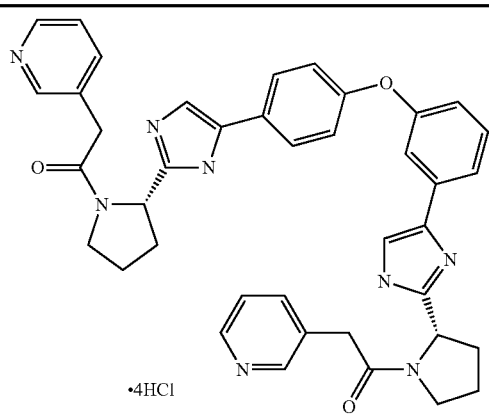

·4HCl

TABLE 1-continued

19

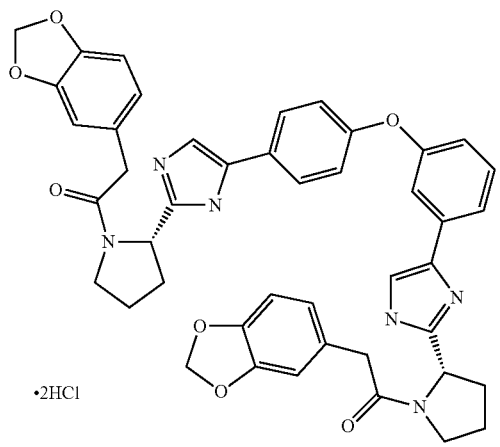 [SMILES: O=C(Cc1ccc2c(c1)OCO2)N1CCC[C@H]1c1nc(-c2cccc(Oc3ccc(-c4cnc([C@@H]5CCCN5C(=O)Cc5ccc6c(c5)OCO6)[nH]4)cc3)c2)c[nH]1]

·2HCl

20

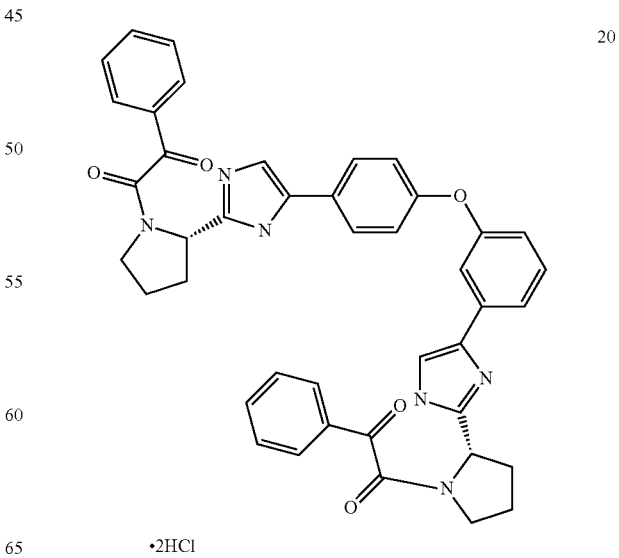

·2HCl

TABLE 1-continued
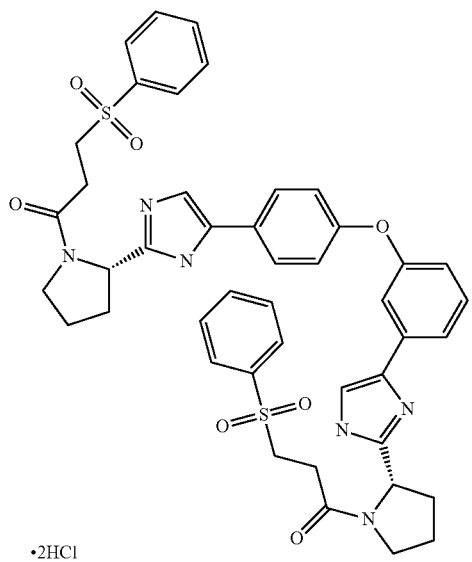 [SMILES: O=C(CCS(=O)(=O)c1ccccc1)N1CCC[C@H]1c1nc(-c2cccc(Oc3ccc(-c4cnc([C@@H]5CCCN5C(=O)CCS(=O)(=O)c5ccccc5)[nH]4)cc3)c2)c[nH]1]
21
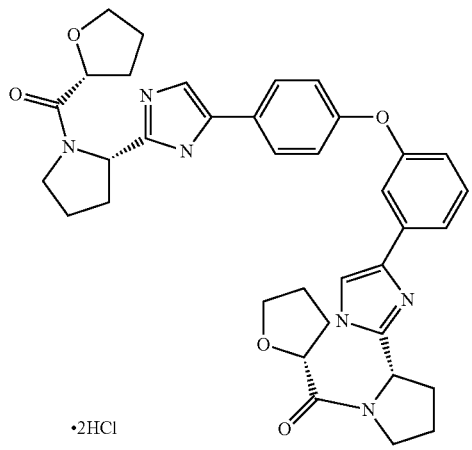 [SMILES: O=C([C@H]1CCCO1)N1CCC[C@H]1c1nc(-c2cccc(Oc3ccc(-c4cnc([C@@H]5CCCN5C(=O)[C@H]5CCCO5)[nH]4)cc3)c2)c[nH]1]
22
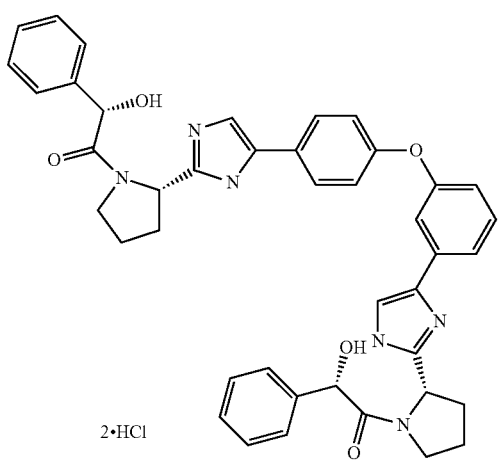 [SMILES: O=C([C@@H](O)c1ccccc1)N1CCC[C@H]1c1nc(-c2cccc(Oc3ccc(-c4cnc([C@@H]5CCCN5C(=O)[C@@H](O)c5ccccc5)[nH]4)cc3)c2)c[nH]1]
23
TABLE 1-continued
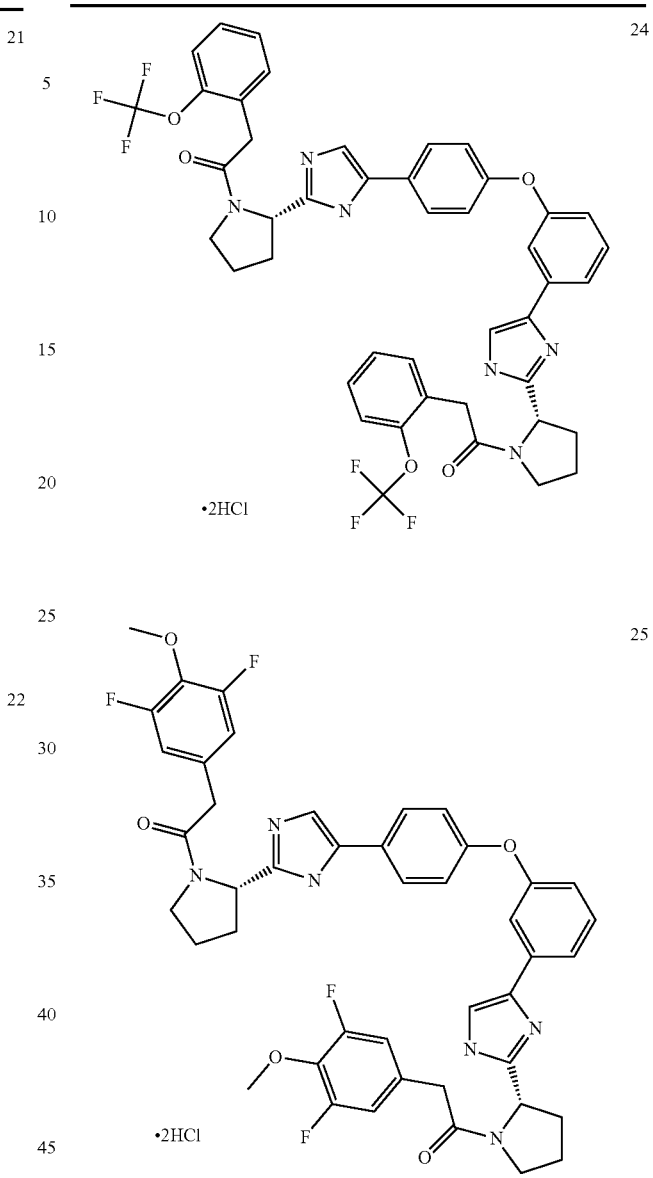
24
25
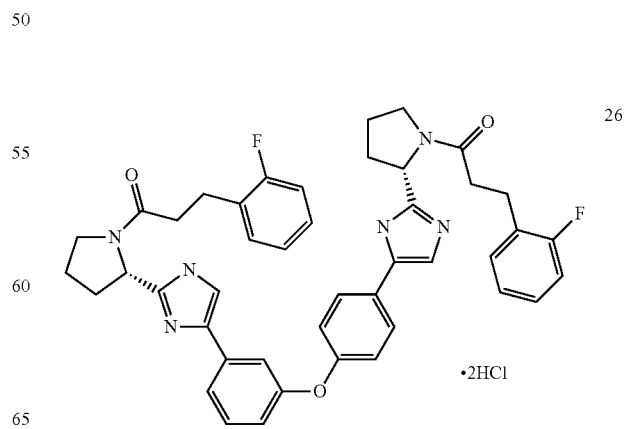
26

TABLE 1-continued
27
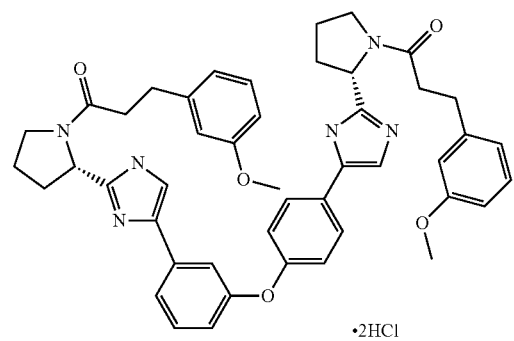 [SMILES: COc1cccc(CCC(=O)N2CCC[C@H]2c2nc(-c3cccc(Oc4ccc(-c5cnc([C@@H]6CCCN6C(=O)CCc6cccc(OC)c6)[nH]5)cc4)c3)c[nH]2)c1]
•2HCl
28
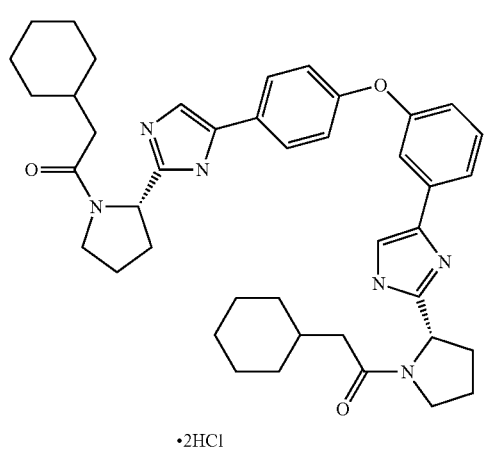 [SMILES: O=C(CC1CCCCC1)N1CCC[C@H]1c1nc(-c2cccc(Oc3ccc(-c4cnc([C@@H]5CCCN5C(=O)CC5CCCCC5)[nH]4)cc3)c2)c[nH]1]
•2HCl
29
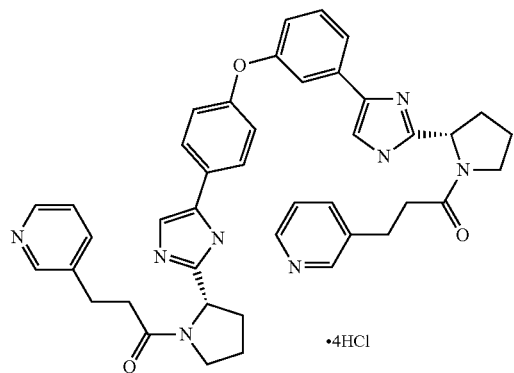 [SMILES: O=C(CCc1cccnc1)N1CCC[C@H]1c1nc(-c2cccc(Oc3ccc(-c4cnc([C@@H]5CCCN5C(=O)CCc5cccnc5)[nH]4)cc3)c2)c[nH]1]
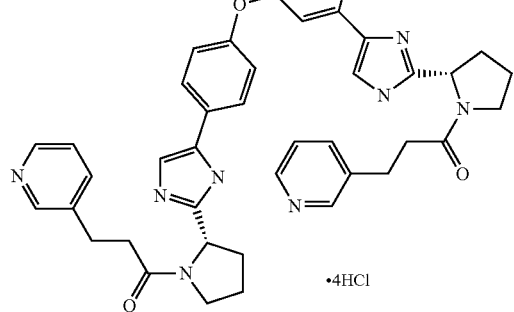
•4HCl
30
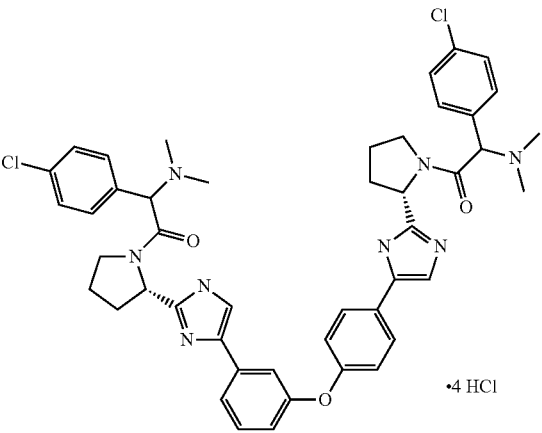 [SMILES: CN(C)C(C(=O)N1CCC[C@H]1c1nc(-c2cccc(Oc3ccc(-c4cnc([C@@H]5CCCN5C(=O)C(c5ccc(Cl)cc5)N(C)C)[nH]4)cc3)c2)c[nH]1)c1ccc(Cl)cc1]
•4 HCl
TABLE 1-continued
31
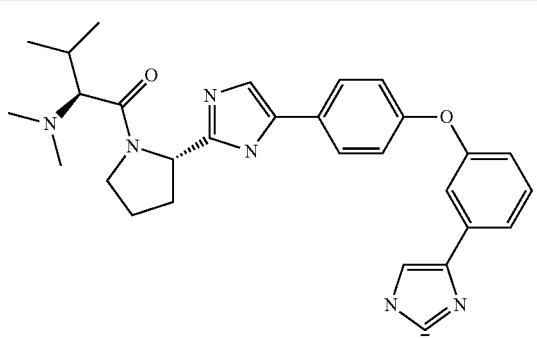
•4HCl
32
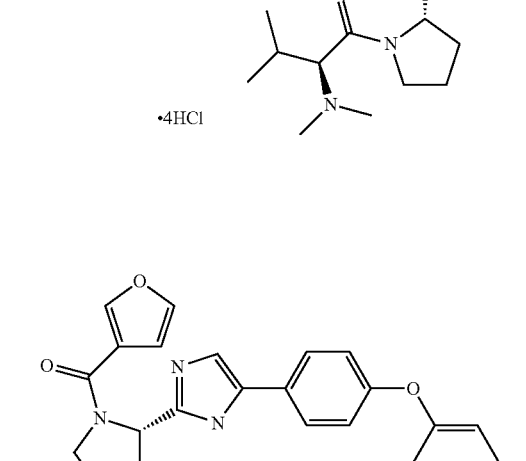
•2HCl
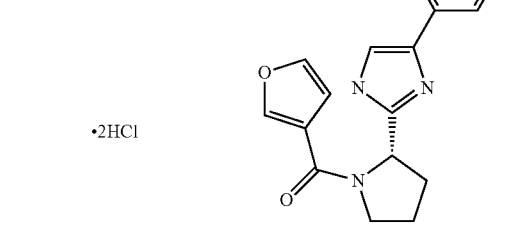
33
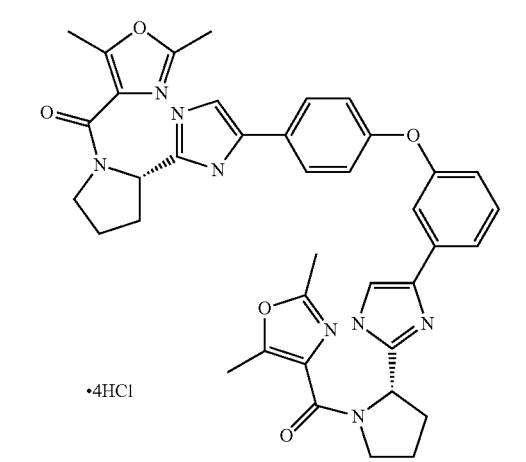 [SMILES: Cc1nc(C(=O)N2CCC[C@H]2c2nc(-c3cccc(Oc4ccc(-c5cnc([C@@H]6CCCN6C(=O)c6nc(C)oc6C)[nH]5)cc4)c3)c[nH]2)c(C)o1]
•4HCl TABLE 1-continued
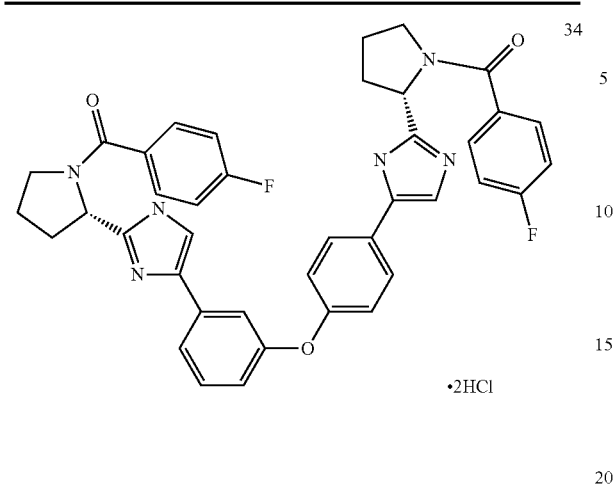
34
•2HCl
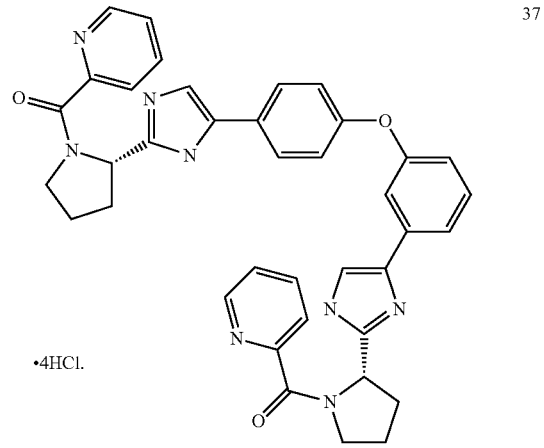
37
•4HCl.
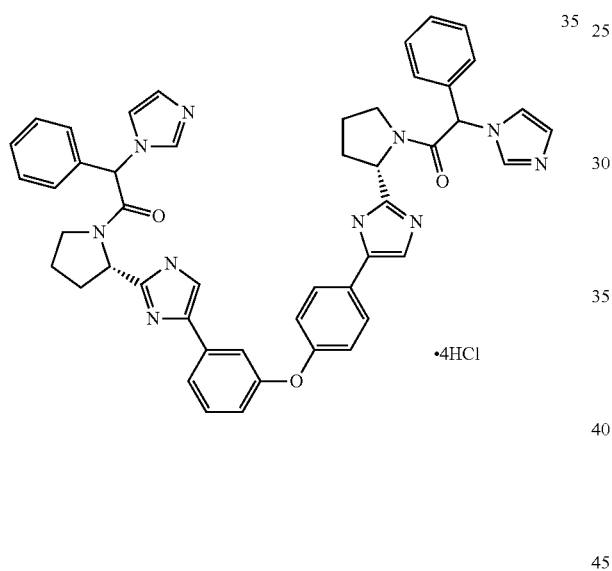
35
•4HCl
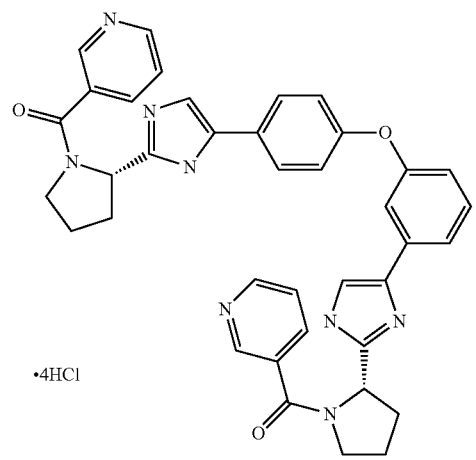 [SMILES: O=C(c1cccnc1)N1CCC[C@H]1c1nc(-c2cccc(Oc3ccc(-c4cnc([C@@H]5CCCN5C(=O)c5cccnc5)[nH]4)cc3)c2)c[nH]1]
38
•4HCl
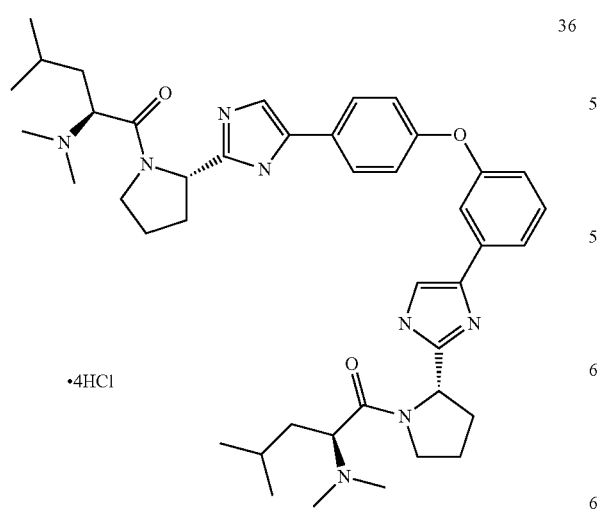
36
•4HCl
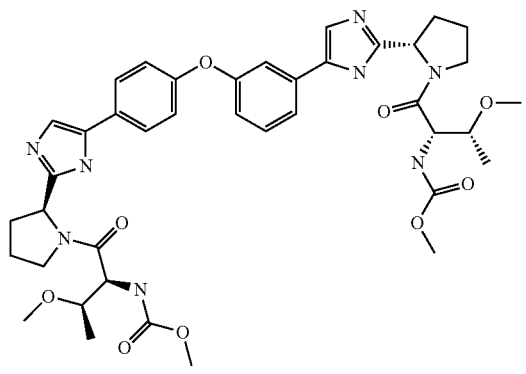 [SMILES: COC(=O)N[C@H](C(=O)N1CCC[C@H]1c1ncc(-c2ccc(Oc3cccc(-c4cnc([C@@H]5CCCN5C(=O)[C@@H](NC(=O)OC)[C@@H](C)OC)[nH]4)c3)cc2)[nH]1)[C@@H](C)OC]
39

TABLE 1-continued

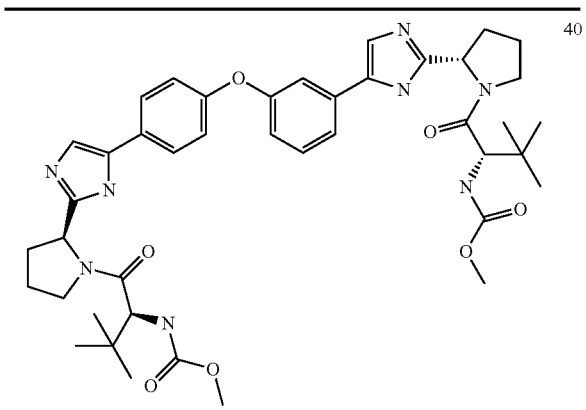

40

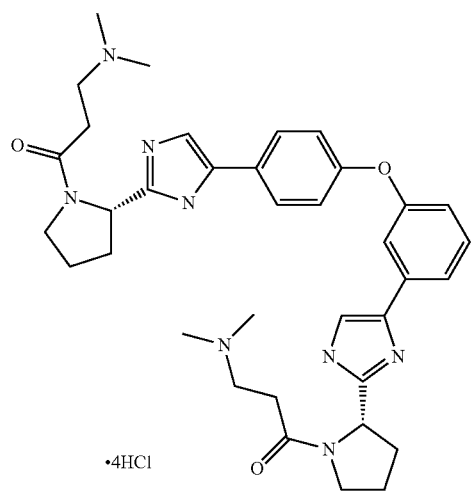 [SMILES: CN(C)CCC(=O)N1CCC[C@H]1c1nc(-c2cccc(Oc3ccc(-c4cnc([C@@H]5CCCN5C(=O)CCN(C)C)[nH]4)cc3)c2)c[nH]1]

41

·4HCl

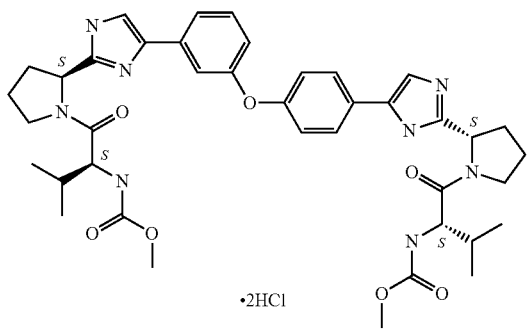

42

·2HCl

TABLE 1-continued

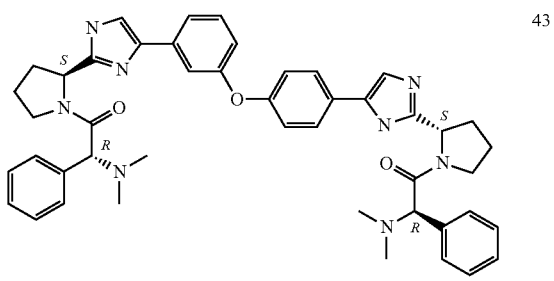

43

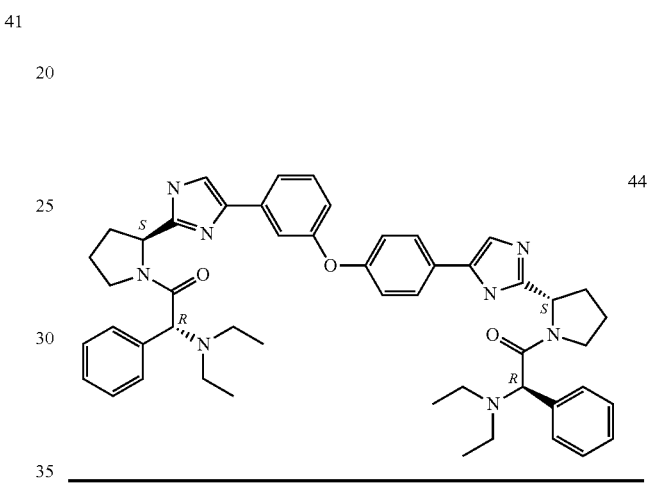

44

Examples 45 to 48

The compounds listed in Table 2 were obtained using the same general procedure as for compounds 18 to 41 above but starting from (S)-tert-butyl 2-(4-(4-(3-(2-((S)-1-(tert-butoxycarbonyl)pyrrolidin-2-yl)-1H-imidazol-4-yl)-4-methoxyphenoxy)phenyl)-1H-imidazol-2-yl)pyrrolidine-1-carboxylate (example 16). Compounds 45, 46, 47 and 48 were further purified by conventional silicagel chromatography (MeOH (7 N NH$_3$)/DCM: 2/98) or reverse phase chromatography.

TABLE 2

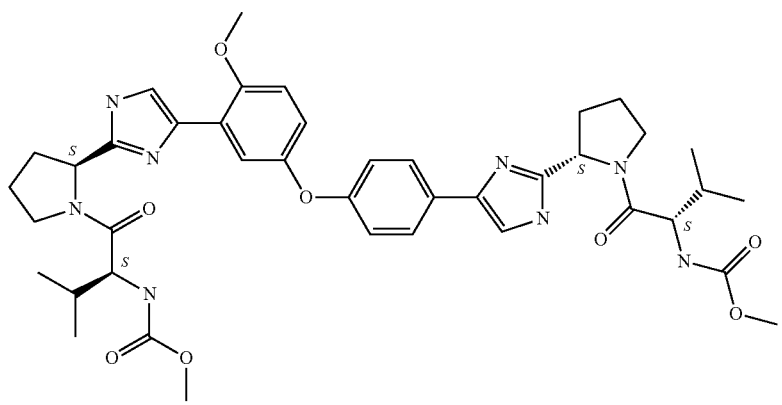

45

TABLE 2-continued
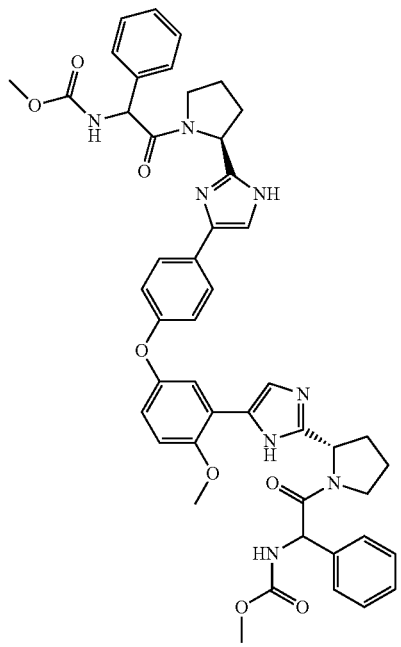 [SMILES: COC(=O)NC(C(=O)N1CCC[C@H]1c1nc(-c2ccc(Oc3ccc(OC)c(-c4cnc([C@@H]5CCCN5C(=O)C(NC(=O)OC)c5ccccc5)[nH]4)c3)cc2)c[nH]1)c1ccccc1]
46
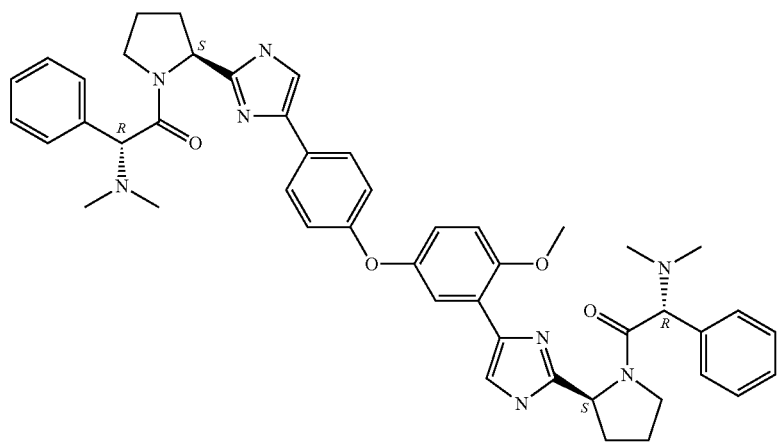
47
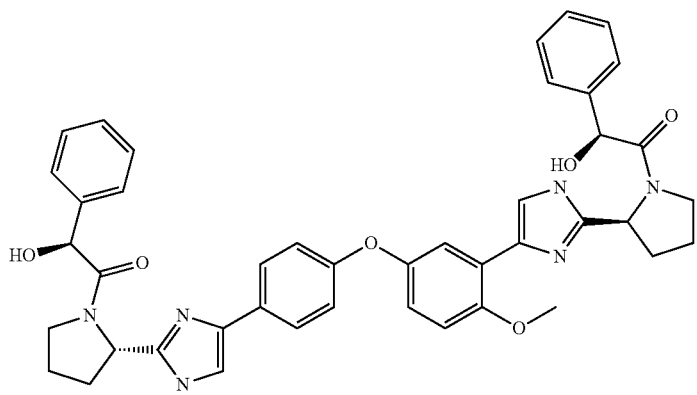 [SMILES: COc1ccc(Oc2ccc(-c3c[nH]c([C@@H]4CCCN4C(=O)[C@@H](O)c4ccccc4)n3)cc2)cc1-c1c[nH]c([C@@H]2CCCN2C(=O)[C@@H](O)c2ccccc2)n1]
48
Example 49
The compound listed in Table 3 was obtained using the same general procedure as for compounds 18 to 41 above but starting from (S)-5,5'-(4,4'-oxybis(4,1-phenylene))-bis(2-((S)-pyrrolidin-2-yl)-1H-imidazole) (Example 15)

TABLE 3

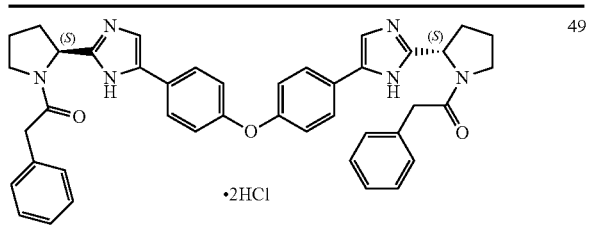

49

All compounds were characterized by LC/MS. The retention times (Rt) for the exemplified compounds are listed in table 3. Table 3 also lists the LC/MS method that was used to determine Rt for each of the exemplified compounds. The following LC/MS methods were used:
Method A: Waters Acquity HPLC equipped with a PDA detector (range 210-400 nm) and a Waters SQD with a dual mode ion source ES+/−. The column used was a Halo C18, 2.7μ, 2.1×50 mm, and held at 50° C. A gradient of 95% aqueous formic acid (0.1%)/5% acetonitrile to 100% acetonitrile was ramped over 1.5 minutes, held for 0.6 minutes, then returns to 100% aqueous formic acid (0.1%) for 0.5 minutes. The flow rate was 0.6 mL/min.
Method B: Liquid Chromatography: Waters Alliance 2695, UV detector: Waters 996 PDA, range: 210-400 nm; Mass detector: Waters ZQ, ion source: ES+, ES− Column used: SunFire C18 3.5μ 4.6×100 mm mobile phase A: 10 mM $NH_4OOCH$+0.1% HCOOH in $H_2O$; mobile phase B: $CH_3OH$; column temp.: 50° C.; flow: 1.5 mL/min gradient time (min) [% A/% B] 0 [65/35] to 7[5/95] to 9.6[5/95] to 9.8[65/35] to 12 [65/35]
Method C: Waters Acquity HPLC equipped with a PDA detector (range 210-400 nm) and a Waters SQD with a dual mode ion source ES+/−. The column used was a XS Strategy 1.7μ, 2.1×20 mm, and held at 50° C. A gradient of 100% aqueous formic acid (0.1%) to 100% acetonitrile was ramped over 1.5 minutes, held for 0.6 minutes, then returns to 100% aqueous formic acid (0.1%) for 0.5 minutes. The flow rate was 0.6 mL/min.

Selected compounds were further characterized by NMR. NMR spectra were recorded on a Bruker Avance 400 spectrometer, operating at 400 MHz for 1H and 100 MHz for 13C and with DMSO as solvent unless otherwise stated. In every case tetramethylsilane (TMS) was used as internal standard. Chemical shifts are given in ppm and J values in Hz.

Multiplicity is indicated using the following abbreviations: d for doublet, t for a triplet, m for a multiplet, etc.

Example 32

$^1$H NMR (600 MHz, DMSO-$d_6$) δ ppm 2.00-2.16 (m, 6 H), 2.42 (m, 2 H), 3.71-3.82 (m, 2 H), 4.03-4.14 (m, 2 H), 5.25-5.41 (m, 1 H), 6.79 (m, 2 H), 7.07-7.14 (m, 1 H), 7.19 (m, 2 H), 7.19 (br. s., 1 H), 7.57 (m, 1 H), 7.67 (m, 1 H), 7.71 (m, 1 H), 7.77 (s, 2 H), 7.90 (m, 2 H), 8.01 (s, 1 H), 8.13 (s, 1 H), 8.28 (br. s., 2 H)

Example 39

$^1$H NMR (600 MHz, DMSO-$d_6$) δ ppm 1.02-1.05 (m, 6 H) 1.88-2.19 (m, 8 H) 3.07-3.13 (m, 3 H) 3.17-3.20 (m, 3 H) 3.37-3.50 (m, 4 H) 3.51-3.56 (m, 6 H) 3.75-3.86 (m, 2 H) 4.20-4.32 (m, 2 H) 4.98-5.10 (m, 2 H) 6.80 (br. s., 1 H) 6.97 (br. s., 2 H) 7.18-7.26 (m, 2 H) 7.29-7.34 (m, 1 H) 7.37 (br. s., 2 H) 7.44-7.52 (m, 2 H) 7.66-7.75 (m, 2 H) 11.63-11.82 (m, 2 H)

Example 40

$^1$H NMR (600 MHz, METHANOL-$d_4$) δ ppm 0.84-1.06 (m, 18 H) 1.81-2.43 (m, 8 H) 3.36-3.44 (m, 2 H) 3.61-3.67 (m, 6 H) 3.78-3.88 (m, 2 H) 3.93-4.03 (m, 2 H) 4.26-4.41 (m, 2 H) 5.05-5.23 (m, 2 H) 6.74-7.08 (m, 4 H) 7.15-7.77 (m, 8 H)

Example 45

$^1$H NMR (600 MHz, DMSO-$d_6$) δ ppm 0.71-0.84 (m, 12 H) 1.92-2.22 (m, 8 H) 2.28-2.41 (m, 2 H) 3.50-3.56 (m, 6 H) 3.78-4.00 (m, 4 H) 3.94-3.99 (m, 3 H) 4.02-4.15 (m, 2 H) 5.11-5.23 (m, 2 H) 7.04-7.13 (m, 2 H) 7.15-7.21 (m, 1 H) 7.22-7.30 (m, 2 H) 7.68-7.75 (m, 1 H) 7.83-7.89 (m, 2 H) 7.83-7.89 (m, 2 H) 7.89-7.93 (m, 1 H) 7.94-7.99 (m, 1 H)

Example 48

1H NMR (600 MHz, DMSO-$d_6$) δ ppm 1.87-2.10 (m, 8 H) 2.29-2.40 (m, 2 H) 3.73-3.89 (m, 4 H) 3.96 (br. s., 3 H) 5.13-5.25 (m, 2 H) 5.30-5.41 (m, 2 H) 7.07-7.13 (m, 2 H) 7.16-7.23 (m, 2 H) 7.24-7.40 (m, 12 H) 7.65-7.98 (m, 5 H)

Biological Examples

Replicon Assay

The compounds of formula (I) were examined for inhibitory activity in the HCV replicon. This cellular assay is based on a bicistronic expression construct, as described by Lohmann et al. (1999) Science vol. 285 pp. 110-113 with modifications described by Krieger et al. (2001) Journal of Virology 75: 4614-4624, in a multi-target screening strategy.

In essence, the method was as follows:
The assay utilized the stably transfected cell line Huh-7 luc/neo (hereafter referred to as Huh-Luc). This cell line harbors an RNA encoding a bicistronic expression construct comprising the wild type NS3-NS5B regions of HCV type Ib translated from an Internal Ribosome Entry Site (IRES) from encephalomyocarditis virus (EMCV), preceded by a reporter portion (FfL-luciferase), and a selectable marker portion (neo$^R$, neomycine phosphotransferase). The construct is flanked by 5' and 3' NTRs (non-translated regions) from HCV type Ib. Continued culture of the replicon cells in the presence of G418 (neo$^R$) is dependent on the replication of the HCV RNA. The stably transfected replicon cells that express HCV RNA, which replicates autonomously and to high levels, encoding inter alia luciferase, were used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which represent the amount of compound required to decrease the level of detected luciferase activity by 50%, or more specifically, to reduce the ability of the genetically linked HCV replicon RNA to replicate.

Results
Table 3 shows the replicon results and cytotoxicity results obtained for compounds of the examples given above.

TABLE 3

| Example number | EC50 (μM) | CC50 (μM) (Huh-7) | Rt (LC/MS method) |
|---|---|---|---|
| 9 | =0.077 | >31.48 | 0.78 (A) |
| 10 | <0.0005 | =4.86 | 0.72 (A) |
| 11 | =6.1803 | >31.48 | 0.66 (A) |
| 18 | 0.0543 | >31.48 | 0.49 (C) |
| 19 | 1.07 | >31.48 | 0.63 (C) |
| 20 | 0.0582 | >31.48 | 0.82 (C) |
| 21 | 3.70 | >31.48 | 0.63 (C) |
| 22 | 1.09 | >31.48 | 0.52 (C) |
| 23 | 0.0608 | 3.66 | 0.75 (A) |
| 24 | 0.0144 | >31.48 | 0.79 (C) |
| 25 | 3.39 | >31.48 | 0.73 (C) |
| 26 | 2.31 | >31.48 | 0.73 (C) |
| 27 | 3.53 | >31.48 | 0.72 (C) |
| 28 | 5.47 | >31.48 | 0.77 (C) |
| 29 | 0.00398 | >31.48 | 0.57 (C) |
| 30 | 0.00362 | 4.6 | 0.54 (C) |
| 31 | 1.16 | 2.87 | 0.50 (C) |
| 32 | 0.978 | >31.48 | 0.54 (C) |
| 33 | 0.864 | >31.48 | 0.58 (C) |
| 34 | 4.34 | >31.48 | 0.63 (C) |
| 35 | 0.00472 | >31.48 | 0.52 (C) |
| 36 | 3.03 | 7.763 | 0.63 (C) |
| 37 | 15.4 | >31.48 | 0.55 (C) |
| 38 | 1.27 | >31.48 | 0.51 (C) |
| 39 | 7.94E−05 | >31.48 | 3.98 (B) |
| 40 | 0.000165 | 12.55 | 5.52 (B) |
| 41 | 1.24 | >31.48 | |
| 42 | 4.33E−05 | 18.59 | 0.60 (C) |
| 43 | 0.000114 | 0.7 | 0.50 (C) |
| 44 | 0.00012 | 0.78 | 2.86 (B) |
| 45 | 0.0627 | 1.66 | |
| 46 | >0.98 | >98.36 | |
| 47 | 0.000705 | | |
| 49 | 1.12 | >31.48 | |

The invention claimed is:

1. A compound of formula I:

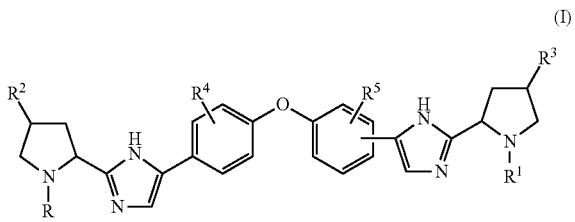

(I)

including any possible stereoisomers thereof, wherein:

R and $R^1$, independently from one another, are benzoyl optionally substituted with one, two or three substituents each independently selected from halo and $C_1$-$C_6$alkyl, or —C(=O)-Het wherein Het is optionally substituted with one or two substituents independently selected from $C_{1-4}$alkyl, or a group of formula —C(=O)—CH($R^x$)—$R^6$, benzyloxycarbonyl, $C_1$-$C_6$alkyloxycarbonyl, a group of formula $H_2N$—CH($R^7$)—C(=O)—, a group of formula $R^8$—O—C(=O)—HN—CH($R^7$)—C(=O)—, or —C(=O)—C(=O)-phenyl;

$R^6$ is $C_1$-$C_4$alkyl, $C_{3-6}$cycloalkyl, benzyl or phenyl wherein the phenyl may be optionally substituted with one, two or three substituents each independently selected from halo, $C_1$-$C_6$alkyl, methoxy, trifluoromethoxy or two substituents on adjacent ring atoms, together with the phenyl ring, form a benzodioxole, and, wherein the $C_1$-$C_4$alkyl is optionally substituted with mono- or di$C_1$-$C_4$alkylamino, phenylsulphonyl, Het, and, wherein benzyl is optionally substituted with one, two or three substituents each independently selected from halo, methoxy;

$R^x$ is selected from hydrogen, hydroxy, $C_1$-$C_6$alkoxy, amino, mono- or di$C_1$-$C_6$alkylamino, pyrrolidinyl, piperidinyl, morpholinyl, imidazolyl, $C_1$-$C_6$alkylcarbonylamino or $C_1$-$C_6$alkyloxycarbonylamino;

Het is a heterocyclic group comprising one or two heteroatoms selected from O and N and having 4 to 7 ring atoms wherein said heterocyclic ring is connected to the carbonyl carbon by a ring carbon atom and wherein at least one of said heteroatoms is adjacent to said ring carbon atom, $R^2$ and $R^3$, independently from one another, are hydrogen, hydroxyl, $C_1$-$C_4$alkyl or halo;

$R^4$ and $R^5$, independently from one another, are hydrogen, $C_1$-$C_4$alkyl, halo or methoxy;

each $R^7$ independently is hydrogen, phenyl, or $C_1$-$C_4$ alkyl optionally substituted with methoxy or phenyl; and, $R^8$ is $C_1$-$C_4$alkyl or benzyl; or a pharmaceutically acceptable salt thereof.

2. The compound of claim 1, wherein $R^2$ and $R^3$ are hydrogen, hydroxy or fluoro, in particular wherein $R^2$ and $R^3$ are hydrogen.

3. The compound of claim 1, wherein R and $R^1$, independently from one another, are a group of formula —C(=O)—CH($R^x$)—$R^6$ or —C(=O)-Het, in particular wherein R and $R^1$, independently from one another, are groups of formula —C(=O)—CH($R^x$)—$R^6$.

4. The compound of claim 1, wherein $R^x$ is hydroxy, $C_1$-$C_6$alkoxy, amino, mono- or di$C_1$-$C_6$alkylamino, pyrrolidinyl, piperidinyl, morpholinyl, $C_1$-$C_6$alkylcarbonylamino or $C_1$-$C_6$alkyloxycarbonylamino; or wherein $R^x$ is hydroxyl, amino, di$C_1$-$C_4$alkylamino, or morpholinyl; or wherein $R^x$ is hydroxy, amino or dimethylamino.

5. The compound of claim 1, wherein $R^6$ is a phenyl ring optionally substituted with one halo or $C_1$-$C_6$alkyl.

6. The compound of claim 1, wherein $R^6$ is selected from phenyl and isopropyl.

7. The compound of claim 1, wherein Het is selected from 2-pyridinyl, 2-pyrimidyl, 2-pyrazinyl, 2-imidazoyl, 2-thiazolyl, 2-thiophenyl, 2-pyrazolinyl, 2-piperidinyl, 2-pyrrolidinyl, 2-pyrrolyl, 2-furanyl, 2-tetrahydrofuranyl, 2-oxetanyl, 2- or 3-morpholinyl, and 2-piperazinyl, in particular 2-tetrahydrofuranyl.

8. The compound of claim 1, wherein $R^4$ and $R^5$ are independently hydrogen, methyl, methoxy or chloro, in particular wherein $R^4$ and $R^5$ are hydrogen.

9. The compound of claim 1, wherein the group

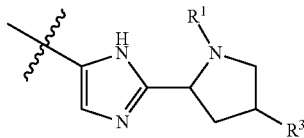

is substituted in meta position relative to the oxygen bridge between the two phenyl groups.

10. A method for inhibiting hepatitis C virus (HCV) replication, comprising contacting a compound according to claim 1 with an HCV.

* * * * *